US012796960B2

(12) United States Patent
Trepanier et al.

(10) Patent No.: US 12,796,960 B2
(45) Date of Patent: Nov. 17, 2026

(54) COMMUNICATION SYSTEM FOR PATIENT SUPPORT APPARATUSES

(71) Applicant: Stryker Corporation, Kalamazoo, MI (US)

(72) Inventors: Jerald A. Trepanier, Kalamazoo, MI (US); Krishna Sandeep Bhimavarapu, Kalamazoo, MI (US); Madhu Thomas, London (CA); Celso Henrique Farnese Pires Pereira, Portage, MI (US); Madhu Sandeep Thota, Portage, MI (US); Thomas Deeds, Northville, MI (US); Kirby M. Neihouser, Portage, MI (US)

(73) Assignee: Stryker Corporation, Portage, MI (US)

( * ) Notice: Subject to any disclaimer, the term of this patent is extended or adjusted under 35 U.S.C. 154(b) by 14 days.

(21) Appl. No.: 18/724,949

(22) PCT Filed: Jun. 7, 2023

(86) PCT No.: PCT/US2023/024644
§ 371 (c)(1),
(2) Date: Jun. 27, 2024

(87) PCT Pub. No.: WO2023/244469
PCT Pub. Date: Dec. 21, 2023

(65) Prior Publication Data

US 2025/0098983 A1 Mar. 27, 2025

Related U.S. Application Data

(60) Provisional application No. 63/352,061, filed on Jun. 14, 2022.

(51) Int. Cl.

| | |
|---|---|
| ***A61B 5/11*** | (2006.01) |
| ***A61B 5/00*** | (2006.01) |
| ***A61G 7/05*** | (2006.01) |

(52) U.S. Cl.
CPC ............ *A61B 5/1115* (2013.01); *A61B 5/746* (2013.01); *A61G 7/05* (2013.01); *A61G 2203/20* (2013.01)

(58) Field of Classification Search
CPC ..................................................... A61B 5/1115
See application file for complete search history.

(56) References Cited

U.S. PATENT DOCUMENTS 1,071,647 A * 8/1913 Alexander ................. F16J 9/16 277/491
7,242,306 B2 7/2007 Wildman et al.
(Continued)

FOREIGN PATENT DOCUMENTS

WO 2009055635 A1 4/2009
WO 2021228946 A1 11/2021
(Continued)

OTHER PUBLICATIONS

International Search Report and Written Opinion, PCT/US23/24644, date Oct. 16, 2023, 19 pages.

*Primary Examiner* — Davetta W Goins
*Assistant Examiner* — Pameshanand Mahase
(74) *Attorney, Agent, or Firm* — Gardner, Linn, Burkhart & Ondersma LLP

(57) ABSTRACT

A patient support apparatus includes a plurality of ultra-wideband transceivers, a display, a controller, and a near field transceiver. The controller is adapted to automatically associate an object with the patient support apparatus when the object is positioned within communication range of the near field transceiver; to use radio frequency (RF) communication between the plurality of ultra-wideband transceivers and the object to determine a position of the object relative to the patient support apparatus; to determine if the object is positioned inside or outside of a volume of space; to automatically disassociate the object from the patient
(Continued)

support apparatus if the object is outside the volume of space; to forward and/or display data from the object if it is associated; and to not forward and/or display data if it is disassociated. The object may be a nurse call device, an exit detection sensor, a second patient support apparatus, etc.

19 Claims, 9 Drawing Sheets

(56) References Cited

U.S. PATENT DOCUMENTS

| | | | | |
|---|---|---|---|---|
| 7,570,152 | B2 | 8/2009 | Smith et al. | |
| 8,082,160 | B2 | 12/2011 | Collins, Jr. et al. | |
| 8,334,777 | B2 | 12/2012 | Wilson et al. | |
| 8,334,779 | B2 | 12/2012 | Zerhusen et al. | |
| 8,552,903 | B2 | 10/2013 | Julian et al. | |
| 8,756,078 | B2 | 6/2014 | Collins, Jr. et al. | |
| 8,786,402 | B2 | 7/2014 | Barnes | |
| 9,320,662 | B2 | 4/2016 | Hayes et al. | |
| 9,375,142 | B2 | 6/2016 | Schultz et al. | |
| 9,427,365 | B2 | 8/2016 | Richards et al. | |
| 9,554,286 | B2 | 1/2017 | Ghabra et al. | |
| 9,569,591 | B2 | 2/2017 | Vanderpohl, III | |
| 9,571,985 | B2 | 2/2017 | Bottazzi et al. | |
| 9,788,151 | B2 | 10/2017 | Duan et al. | |
| 10,064,012 | B1 * | 8/2018 | Boston | G01S 1/0428 |
| 10,258,538 | B2 | 4/2019 | Barta et al. | |
| 10,474,808 | B2 | 11/2019 | Huster | |
| 10,486,646 | B2 | 11/2019 | Ledvina et al. | |
| 10,608,699 | B2 | 3/2020 | Nabki et al. | |
| 10,759,389 | B2 | 9/2020 | Ledvina et al. | |
| 10,811,136 | B2 | 10/2020 | Bhimavarapu et al. | |
| 10,818,163 | B2 | 10/2020 | Huster | |
| 10,846,961 | B2 | 11/2020 | de Perthuis et al. | |
| 11,019,195 | B2 | 5/2021 | Ledvina et al. | |
| 11,026,067 | B2 | 6/2021 | Martin et al. | |
| 11,082,809 | B1 | 8/2021 | Burowski et al. | |
| 11,153,810 | B2 | 10/2021 | Yoon et al. | |
| 11,172,892 | B2 | 11/2021 | Zerhusen et al. | |
| 11,177,026 | B2 | 11/2021 | Heavelyn et al. | |
| 11,289,194 | B1 | 3/2022 | Pipher et al. | |
| 11,301,651 | B2 | 4/2022 | Studerus et al. | |
| 11,343,645 | B2 | 5/2022 | Yoon et al. | |
| 11,400,889 | B2 | 8/2022 | Parthasarathi et al. | |
| 11,610,671 | B2 | 3/2023 | Hochworter | |
| 11,638,233 | B2 | 4/2023 | Shin et al. | |
| 2007/0268119 | A1 * | 11/2007 | Cram | B60Q 9/00 340/457 |
| 2008/0312971 | A2 | 12/2008 | Rosow et al. | |
| 2011/0208541 | A1 | 8/2011 | Wilson et al. | |
| 2014/0297327 | A1 | 10/2014 | Heil et al. | |
| 2014/0320290 | A1 | 10/2014 | Reeder et al. | |
| 2016/0140307 | A1 | 5/2016 | Brosnan et al. | |
| 2017/0176240 | A1 * | 6/2017 | Paul | G01G 19/44 |
| 2017/0287316 | A1 | 10/2017 | Wildman et al. | |
| 2018/0036544 | A1 | 2/2018 | Delisle et al. | |
| 2018/0125414 | A1 * | 5/2018 | Lafleche | A61G 7/05776 |
| 2019/0046379 | A1 * | 2/2019 | Constant | G16H 40/63 |
| 2019/0150737 | A1 * | 5/2019 | Bodurka | A61G 7/018 |
| 2020/0051405 | A1 * | 2/2020 | Bhimavarapu | G08B 5/228 |
| 2020/0064182 | A1 * | 2/2020 | Lin | G01G 23/36 |
| 2020/0186518 | A1 * | 6/2020 | Shah | H04L 67/06 |
| 2020/0205661 | A1 | 7/2020 | Bostic et al. | |
| 2021/0014677 | A1 | 1/2021 | Han et al. | |
| 2021/0065885 | A1 | 3/2021 | Receveur et al. | |
| 2021/0266710 | A1 | 8/2021 | Martin et al. | |
| 2021/0360366 | A1 | 11/2021 | Bailey et al. | |
| 2021/0400439 | A1 | 12/2021 | Troester et al. | |
| 2022/0053292 | A1 | 2/2022 | Hoff et al. | |
| 2022/0137204 | A1 | 5/2022 | Nguyen et al. | |
| 2022/0139133 | A1 | 5/2022 | Schober et al. | |
| 2022/0148406 | A1 | 5/2022 | Bhimavarapu et al. | |
| 2022/0208372 | A1 | 6/2022 | Bodurka et al. | |
| 2022/0241124 | A1 | 8/2022 | Bhimavarapu et al. | |
| 2022/0287897 | A1 | 9/2022 | Bhimavarapu et al. | |
| 2023/0337941 | A1 | 10/2023 | Pereira et al. | |

FOREIGN PATENT DOCUMENTS

| | | | |
|---|---|---|---|
| WO | 2021236649 | A1 | 11/2021 |
| WO | 2022086515 | A1 | 4/2022 |

* cited by examiner

COMMUNICATION SYSTEM FOR PATIENT SUPPORT APPARATUSES

BACKGROUND

The present disclosure relates to patient support apparatuses, such as beds, cots, stretchers, recliners, or the like. More specifically, the present disclosure relates to patient support apparatuses that communicate with one or more devices that are separate from the patient support apparatus itself.

SUMMARY

According to the various aspects described herein, the present disclosure is directed to a patient support apparatus system that helps track the location of assets within a healthcare facility, that helps patients communicate with nurses when the patients are mobile, that helps alert caregivers when patient's exit from patient support apparatuses, and that helps reduce the workload of caregivers in assisting in the recovery of their patients. The system automatically associates assets within a healthcare facility with a particular patient support apparatus, patient, and/or room, and allows patients to summon nurses when the patient is positioned outside of their bed, such as in a recliner or other secondary patient support apparatus. In some embodiments, the system includes a mobile nurse call device that can be attached to patient support apparatuses, thereby giving the patient support apparatus a nurse call communication ability. In some embodiments, the system includes a mobile exit detection pad that can be placed on a patient support apparatus, thereby giving the patient support apparatus an exit detection capability. The exit detection capability includes the ability to communicate an exit detection alert to a remote location through an existing nurse call system. These and other aspects of the present disclosure will be apparent to a person of ordinary skill light of the following written description and accompanying drawings.

According to a first aspect of the present disclosure, a patient support apparatus is provided that includes a support surface adapted to support a patient, a first transceiver coupled to a first location on the patient support apparatus, a second transceiver coupled to a second location on the patient support apparatus, a third transceiver coupled to a third location on the patient support apparatus, and a controller. The controller is adapted to use radio frequency (RF) communication between the first, second, and third transceivers and an exit detection sensor to determine a position of the exit detection sensor relative to the patient support apparatus. The controller is further adapted to receive an exit detection alert signal from the exit detection sensor, to determine if the exit detection sensor is positioned inside or outside of a volume of space, and, if the exit detection sensor is positioned inside the volume of space, to transmit an exit detection alert to an off-board recipient in response to receiving the exit detection alert signal from the exit detection sensor.

According to another aspect of the present disclosure, a patient support apparatus is provided that includes a support surface adapted to support a patient, a display, a first transceiver coupled to a first location on the patient support apparatus, a second transceiver coupled to a second location on the patient support apparatus, a third transceiver coupled to a third location on the patient support apparatus, and a controller. The controller is adapted to use radio frequency (RF) communication between the first, second, and third transceivers and a second patient support apparatus to determine a position of the second patient support apparatus relative to the patient support apparatus. The controllers is further adapted to determine if the second patient support apparatus is positioned inside or outside of a volume of space, to receive data from the second patient support apparatus, and, if the second patient support apparatus is positioned inside the volume of space, to perform at least one of the following: to forward the data to an off-board recipient, or to display the data on the display.

According to another aspect of the present disclosure, a patient support apparatus is provided that includes a support surface adapted to support a patient, a first transceiver coupled to a first location on the patient support apparatus, a second transceiver coupled to a second location on the patient support apparatus, a third transceiver coupled to a third location on the patient support apparatus, and a controller. The controller is adapted to use radio frequency (RF) communication between the first, second, and third transceivers and an object to determine a first position of the object relative to the patient support apparatus. The controller is further adapted to determine if the object is positioned inside or outside of a first volume of space; to use RF communication between the first, second, and third transceivers and a fixed locator to determine a second position of the patient support apparatus relative to the fixed locator; to determine if both the patient support apparatus and the fixed locator are positioned inside or outside of a second volume of space; and, if both the object is positioned inside the first volume of space and the fixed locator and patient support apparatus are positioned inside of the second volume of space, to forward location information to a server indicating a location of the object within a healthcare facility.

According to still another aspect of the present disclosure, a patient support apparatus is provided that includes a support surface adapted to support a patient, a display, a plurality of ultra-wideband transceivers, a near field transceiver, and a controller. The controller is adapted to automatically associate an object with the patient support apparatus when the object is positioned within communication range of the near field transceiver. The controller is further adapted to use radio frequency (RF) communication between the plurality of ultra-wideband transceivers and the object to determine a position of the object relative to the patient support apparatus; to determine if the object is positioned inside or outside of a volume of space; to automatically disassociate the object from the patient support apparatus if the object is positioned outside of the volume of space; to not forward data received from the object to the off-board recipient when the object is disassociated from the patient support apparatus; and to perform at least one of the following when the object is associated with the patient support apparatus: (a) forward data received from the object to an off-board recipient, or (b) display data received from the object on the display.

According to still other aspects of the present disclosure, the patient support apparatus may comprise a nurse call system interface adapted to communicate with a nurse call system outlet integrated into a wall of a healthcare facility. The nurse call system outlet includes a plurality of electrical pins and the controller is adapted to transmit the exit detection alert to the off-board recipient by changing an electrical state of a pin of the nurse call system outlet.

In some aspects, the nurse call system interface is adapted to communicate with the nurse call system outlet by wireless or wired communication.

The controller, in some aspects, is further adapted to use radio frequency (RF) communication between the first, second, and third transceivers and a second patient support apparatus to determine if the second patient support apparatus is positioned inside or outside of a second volume of space.

In some aspects, the exit detection sensor includes a pressure sensing pad adapted to be positioned underneath the patient. The pressure sensing pad may be adapted to be removable from the patient support apparatus and positioned on a support surface of second patient support apparatus.

In some aspects, the first transceiver, the second transceiver, and the third transceiver are all ultra-wideband transceivers. Additional, or fewer, ultra-wideband transceivers may also, or alternatively, be included on the patient support apparatus.

The patient support apparatus, in some aspects, further includes a memory in which the first location, the second location, and the third location of the first, second, and third transceivers, respectively, is stored.

The controller, in some aspects, is further adapted to use the stored locations of the first, second, and third transceivers to determine whether the exit detection sensor is positioned inside or outside of the volume of space.

The controller, in some aspects, is further adapted, if the exit detection sensor is positioned outside the volume of space, to not transmit the exit detection alert to the off-board recipient in response to receiving the exit detection alert signal from the exit detection sensor.

The controller, in some aspects, is further adapted to use RF communication between the first, second, and third transceivers and a fixed locator to determine a position of the patient support apparatus relative to the fixed locator.

In some aspects, the controller is further adapted to receive an identifier from the fixed locator, to determine if the patient support apparatus is positioned within a threshold distance to the fixed locator, and to forward the fixed locator identifier to a server if the patient support apparatus is positioned within the threshold distance.

The off-board recipient, in some aspects, includes the fixed locator if the patient support apparatus is positioned within the threshold distance.

The patient support apparatus, in some aspects, further includes a microphone adapted to convert sounds of the patient's voice to audio signals, and the controller is further adapted to transmit the audio signals to the fixed locator if the fixed locator is positioned within the threshold distance, and to not transmit the audio signals to the fixed locator if the fixed locator is positioned outside of the threshold distance.

The off-board recipient, in some aspects, is a nurse call system outlet integrated into a wall of a healthcare facility.

In some aspects, the controller is further adapted to use radio frequency (RF) communication between the first, second, and third transceivers and an object to determine a second position of the object relative to the patient support apparatus; to determine if the object is positioned inside or outside of a second volume of space; to use RF communication between the first, second, and third transceivers and a fixed locator to determine a third position of the patient support apparatus relative to the fixed locator; to determine if both the patient support apparatus and the fixed locator are positioned inside or outside of a third volume of space; and, if both the object is positioned inside the second volume of space and the fixed locator and the patient support apparatus are positioned inside of the third volume of space, to forward location information to a server indicating a location of the object within a healthcare facility.

In some aspects, the controller is further adapted to use the position of the exit detection sensor and the second position of the object to determine if the exit detection sensor is coupled to the object.

The location information, in some aspects, indicates that the object and the patient support apparatus are positioned in a common room of the healthcare facility.

The controller, in some aspects, is further adapted to use radio frequency (RF) communication between the first, second, and third transceivers and a tag coupled to a nurse call device to determine a position of the nurse call device relative to the patient support apparatus. The controller may further be adapted to receive a nurse call signal from the nurse call device; to determine if the nurse call device is positioned inside or outside of the volume of space; and, if the nurse call device is positioned inside the volume of space, to transmit the nurse call signal to a nurse call system in response to receiving the nurse call signal from the nurse call device.

The patient support apparatus may further include a nurse call system interface adapted to communicate with a nurse call system outlet integrated into a wall of a healthcare facility, wherein the nurse call system outlet includes a plurality of electrical pins and the controller is adapted to transmit the nurse call signal to the nurse call system by changing an electrical state of a pin of the nurse call system outlet.

The patient support apparatus, in some aspects, includes a first near field transceiver adapted to read data from a second near field transceiver coupled to the tag.

The controller, in some aspects, is further adapted to automatically associate the tag to the patient support apparatus when the tag is positioned close enough to the patient support apparatus for the first and second near field transceivers to communicate with each other.

The controller, in some aspects, is further adapted to automatically disassociate the tag from the patient support apparatus when the tag is moved outside of the volume of space.

In some aspects, the controller is further adapted, if the tag is disassociated from the patient support apparatus, to not transmit the nurse call signal to the nurse call system in response to receiving the nurse call signal from the nurse call device.

The controller, in some aspects, is adapted to display a first message on the display when the controller associates the tag to the patient support apparatus, and to display a second message on the display when the controller disassociates the tag from the patient support apparatus.

The patient support apparatus, in some aspects, further includes a fourth transceiver adapted to communicate with a fifth transceiver coupled to the tag, wherein the controller is further adapted to perform the following: (a) when the tag is associated with the patient support apparatus, to forward audio signals received from the tag via the fourth transceiver to a nurse call system outlet; and (b) when the tag is disassociated from the patient support apparatus, to not forward audio signals from the tag to the nurse call system outlet.

In some aspects, the patient support apparatus further includes a plurality of siderails and a footboard, and the first near field transceiver is integrated into one of the siderails or the footboard.

The controller, in some aspects, is further adapted to receive an ID from the second patient support apparatus, to check to see if the ID matches a criterion, to forward the data to the off-board recipient if the ID matches the criterion and the second patient support apparatus is positioned inside the volume of space, and to not forward the data to the off-board recipient if the ID does not match the criterion.

The off-board recipient, in some aspects, includes the fixed locator if the patient support apparatus is positioned within the threshold distance.

The data, in some aspects, includes an exit detection alert signal.

The patient support apparatus, in some aspects, is a bed and the second patient support apparatus is a recliner.

The data, in some aspects, includes at least one of the following: a brake status of the second patient support apparatus, a lock status of a lock of the second patient support apparatus, an angle of a component of the second patient support apparatus, an error message, or an occupancy detection signal.

The second patient support apparatus, in some aspects, includes an exit detection sensor that includes a pressure sensing pad adapted to be positioned underneath the patient.

The pressure sensing pad, in some aspects, is adapted to be removable from the second patient support apparatus and positioned on a support surface of another patient support apparatus.

The patient support apparatus, in some aspects, further includes a network transceiver adapted to communicate with a computer network of a healthcare facility in which the patient support apparatus is positioned. The off-board recipient may be a server in communication with the computer network.

In some aspects, the first, second, and third transceivers are ultra-wideband transceivers adapted to communicate with a fourth ultra-wideband transceiver coupled to the second patient support apparatus.

The fourth ultra-wideband transceiver, in some aspects, is incorporated into a removable tag coupled to the second patient support apparatus.

In some aspects, the controller is further adapted to both forward the data to the off-board recipient and to display the data on the display if the second patient support apparatus is positioned inside the volume of space.

In some aspects, the controller is further adapted to not forward the location information to the server if either or both of the following are true: (a) the second patient support apparatus or object is positioned outside of the volume of space; or (b) the fixed locator and the patient support apparatus are not both positioned inside the second volume of space.

In some aspects, the location information includes a first ID received from the object and a second ID received from the fixed locator. The second ID corresponds to a particular location of the fixed locator within the healthcare facility.

In some aspects, the first volume of space and the second volume of space are both defined in a fixed relationship to the patient support apparatus.

In some aspects, the first volume of space is defined in a fixed relationship to the patient support apparatus and the second volume of space is defined in a fixed relationship to the fixed locator.

The object, in some aspects, is a mobile object adapted to assist in caring for the patient.

The object, in some aspects, is a recliner.

The controller, in some aspects, is further adapted to receive data from the object.

The data, in some aspects, includes an exit detection alert signal and/or a nurse call signal.

The object, in some aspects, is a second patient support apparatus and the data includes an exit detection alert signal.

The object, in some aspects, is a nurse call device and the data includes a nurse call signal.

The patient support apparatus, in some aspects, includes a Bluetooth transceiver, and the controller is further adapted to perform the following: (a) when the nurse call device is associated with the patient support apparatus, to receive audio signals from the nurse call device via the Bluetooth transceiver and to forward the audio signals to the nurse call system outlet via the nurse call system interface; and (b) when the nurse call device is disassociated with the patient support apparatus, to not forward any audio signals from the nurse call device to the nurse call system outlet.

The object, in some aspects, is a device adapted to improve a mobility level of the patient.

The object, in some aspects, is a tag adapted to be attached to a second patient support apparatus.

The tag, in some aspects, includes an adhesive adapted to allow the tag to be releasably secured to the second patient support apparatus.

The tag, in some aspects, includes a button adapted to be pressed by the patient, and the tag is adapted to transmit a nurse call signal to the patient support apparatus in response to the button being pressed.

The object, in some aspects, includes an exit detection sensor.

The exit detection sensor, in some aspects, is a pressure sensing pad adapted to be positioned underneath the patient.

In some aspects, the controller is further adapted to use RF communication between the plurality of ultra-wideband transceivers and a fixed locator to determine a second position of the patient support apparatus relative to the fixed locator; to associate the fixed locator to the patient support apparatus if the patient support apparatus and the fixed locator are both positioned inside of a second volume of space; and to disassociate the fixed locator from the patient support apparatus if the patient support apparatus and fixed locator are not both positioned inside of the second volume of space.

In some aspects, the controller is further adapted to perform the following: (a) if the object is associated with the patient support apparatus, to forward location information to a server indicating a location of the object within a healthcare facility; and (b) if the object is disassociated from the patient support apparatus, to not forward the location information to the server.

Before the various aspects of the disclosure are explained in detail, it is to be understood that the claims are not to be limited to the details of operation or to the details of construction and the arrangement of the components set forth in the following description or illustrated in the drawings. The aspects described herein are capable of being practiced or being carried out in alternative ways not expressly disclosed herein. Also, it is to be understood that the phraseology and terminology used herein are for the purpose of description and should not be regarded as limiting. The use of “including” and “comprising” and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
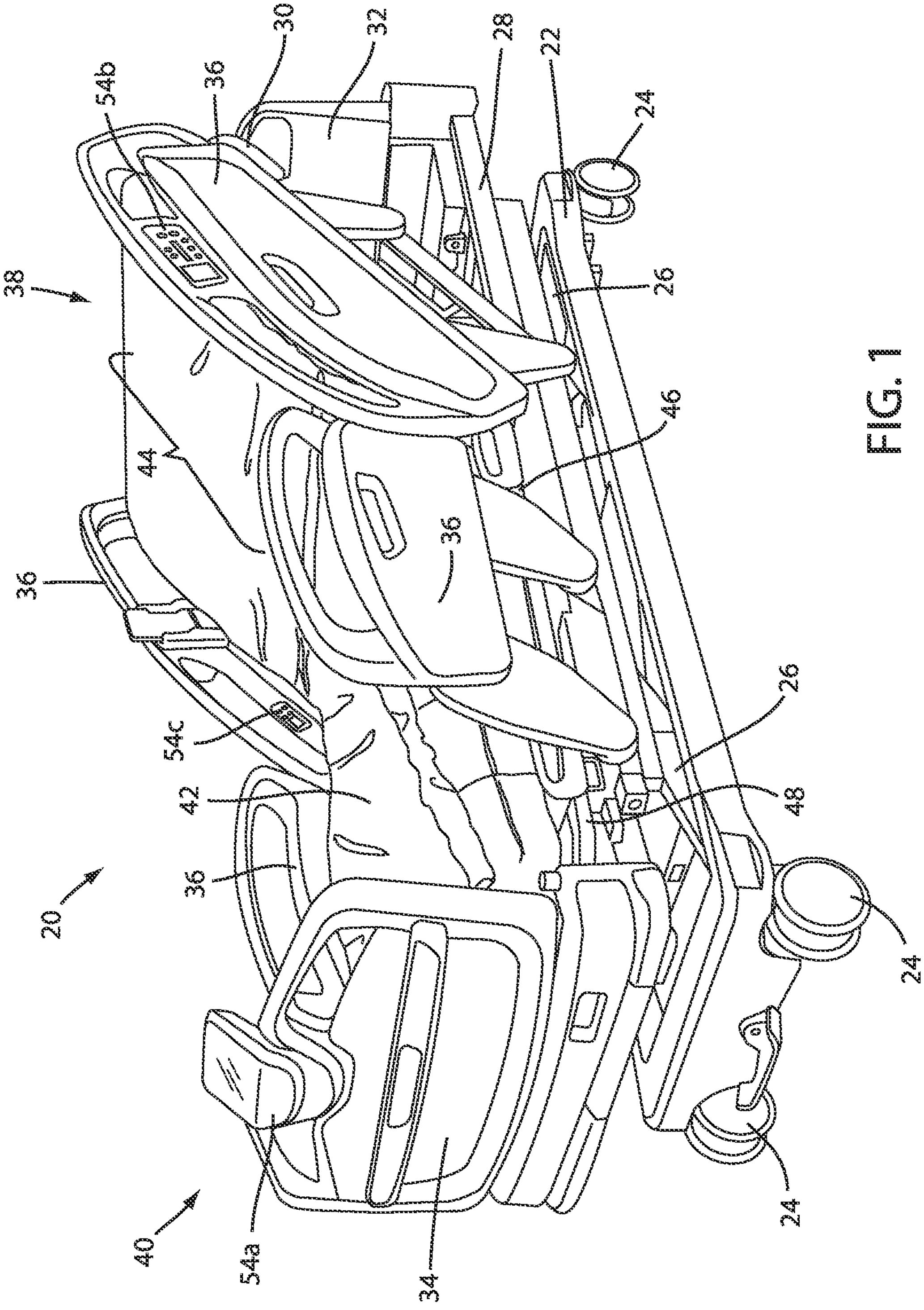
FIG. 1 is a perspective view of a patient support apparatus according to a first aspect of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. In some embodiments, the mattress 42 includes one or more inflatable bladders that are controllable via a blower, or other source of pressurized air. In at least one embodiment, the inflation of the bladders of the mattress 42 is controllable via electronics built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions that are different from what is shown in the attached drawings, such as, but not limited to, the construction described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the mechanical construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of mechanical constructions, such as, but not limited to, those described in commonly assigned, U.S. Pat. No. 7,690,059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall mechanical construction of patient support apparatus 20 may also take on still other forms different from what is disclosed in the aforementioned references provided the patient support apparatus includes one or more of the functions, features, and/or structures discussed in greater detail below.

Figure 2:
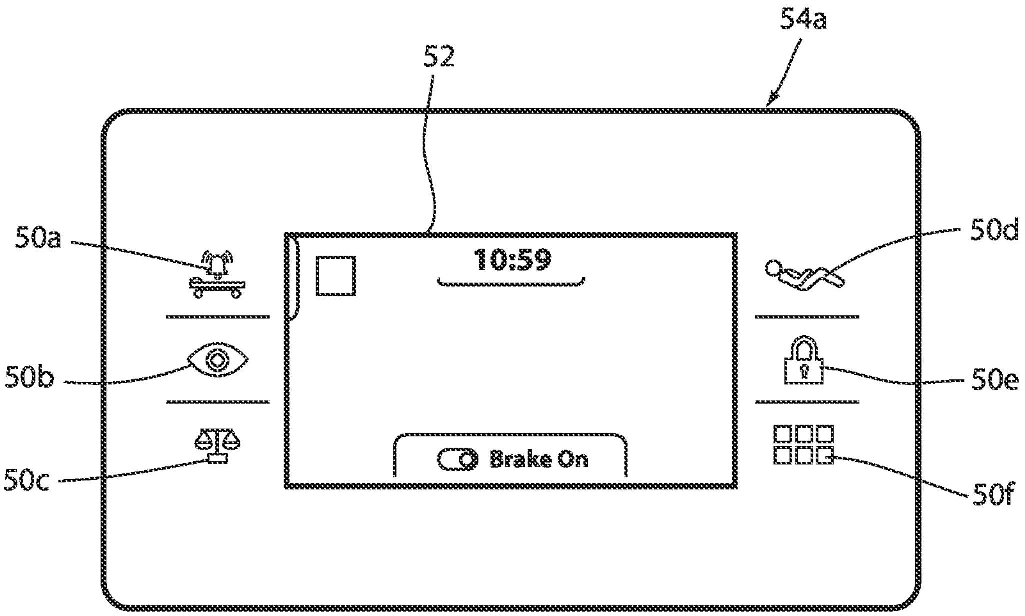
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54*a*, a pair of outer siderail control panels 54*b* (only one of which is visible), and a pair of inner siderail control panels 54*c* (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54*a* allow a user to control one or more of the following: change a height of support deck 30; raise or lower head section 44; activate and deactivate a brake for wheels 24; arm and disarm an exit detection system 136 (FIG. 5); change various settings on patient support apparatus 20; view the current location of the patient support apparatus 20 as determined by the location detection system discussed herein; view what devices, such as, but not limited to, nurse call devices, exit detection sensors, secondary patient support apparatuses, medical devices, etc. that the patient support apparatus 20 has associated itself with; and perform other actions. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Figure 5:
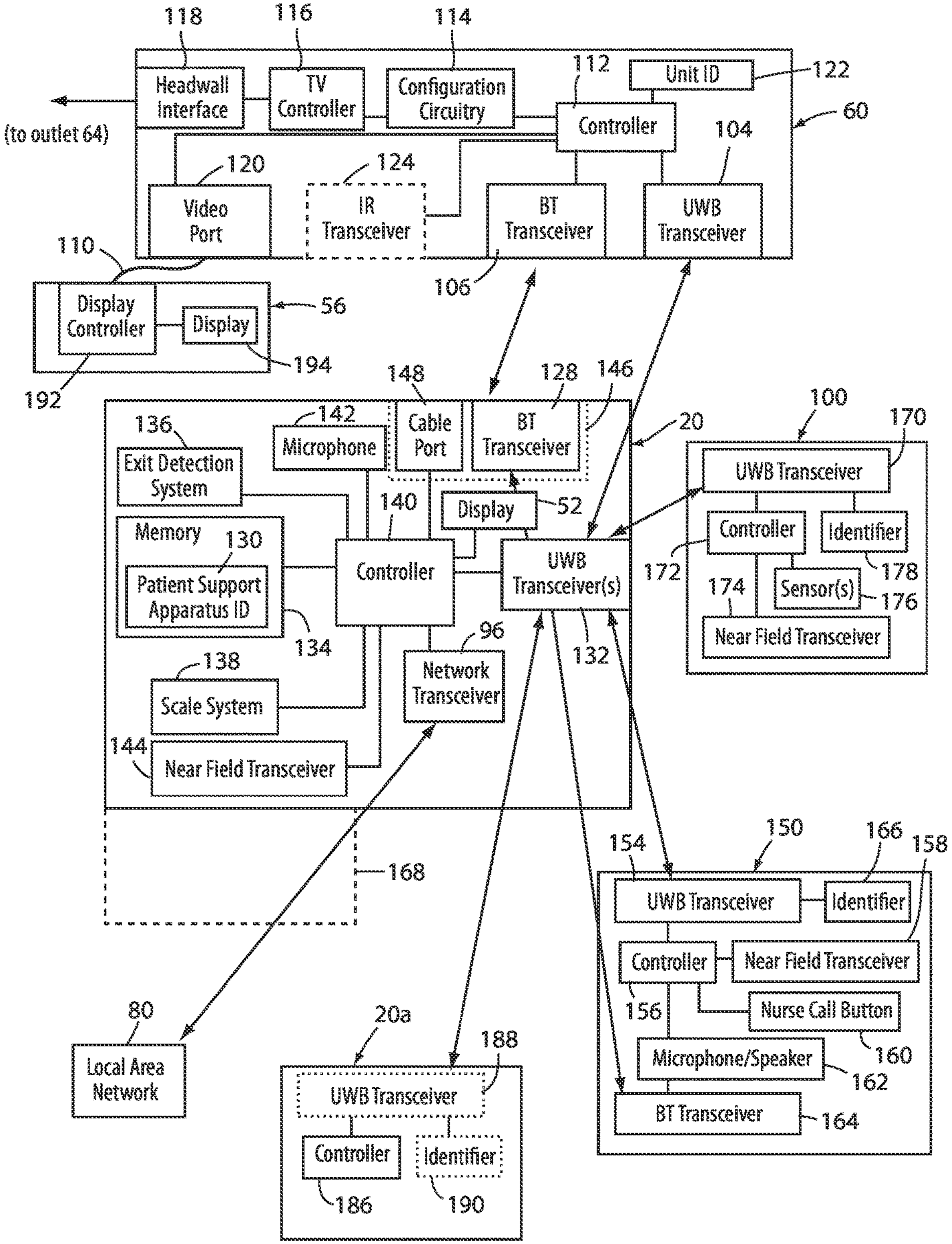
FIG. 5 is a block diagram of the patient support apparatus, the second patient support apparatus, a portable exit detection sensor, a portable nurse call device, the display device, and the healthcare facility network.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system 136 (FIG. 5). The exit detection system 136 is as adapted to issue an alert when a patient exits from patient support apparatus 20. Exit detection system 136 may include any of the same features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

When a user presses navigation control 50*b* (FIG. 2), control panel 54 displays a monitoring control screen that includes a plurality of control icons that, when touched, control an onboard monitoring system built into patient support apparatus 20. The onboard monitoring system alerts the caregiver through a unified indicator, such as a light or a plurality of lights controlled in a unified manner, when any one or more of a plurality of settings on patient support apparatus 20 are in an undesired state, and uses that same unified indicator to indicate when all of the plurality of settings are in their respective desired states. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

When a user presses navigation control 50*c*, control panel 54*a* displays a scale control screen that includes a plurality of control icons that, when touched, control a scale system 138 (FIG. 5) of patient support apparatus 20. Such a scale system 138 may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors and/or other components that are utilized by the exit detection system 136, or it may utilize one or more different sensors and/or other components. Other scale systems besides those mentioned above in the '254 and '954 applications may alternatively be included within patient support apparatus 20.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50*e*, control panel 54*a* displays a motion lock control screen that includes a plurality of control icons that, when touched, control one or more motion lockout functions of patient support apparatus 20. Such motion lockout functions typically include the ability for a caregiver to use control panel 54*a* to lock out one or more of the motion controls 50 of the patient control panels 54*c* such that the patient is not able to use those controls 50 on control panels 54*c* to control the movement of one or more components of patient support apparatus 20. The motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, displaying information about one or more devices that are currently associated with patient support apparatus 20, diagnostic and/or service information for patient support apparatus 20, mattress control and/or status information, configuration settings, location information, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 50*f* allows a user to navigate to a screen that enables a user to see which devices, if any, are currently located within a predefined volume of space that encompasses patient support apparatus 20. As will be discussed in greater detail below, patient support apparatus 20 includes an onboard locating system that is adapted to automatically determine the relative position of one or more devices with respect to patient support apparatus 20 and, in some instances, automatically associate those devices with patient support apparatus 20 (and/or the patient assigned to patient support apparatus 20) depending upon the proximity of the medical device to patient support apparatus 20. Further details of this locating system are provided below.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* could alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls. Additionally, patient support apparatus 20 may be modified to include additional, fewer, and/or different navigation controls from the navigation controls 50*a-f* shown in FIG. 2.

Figure 3:
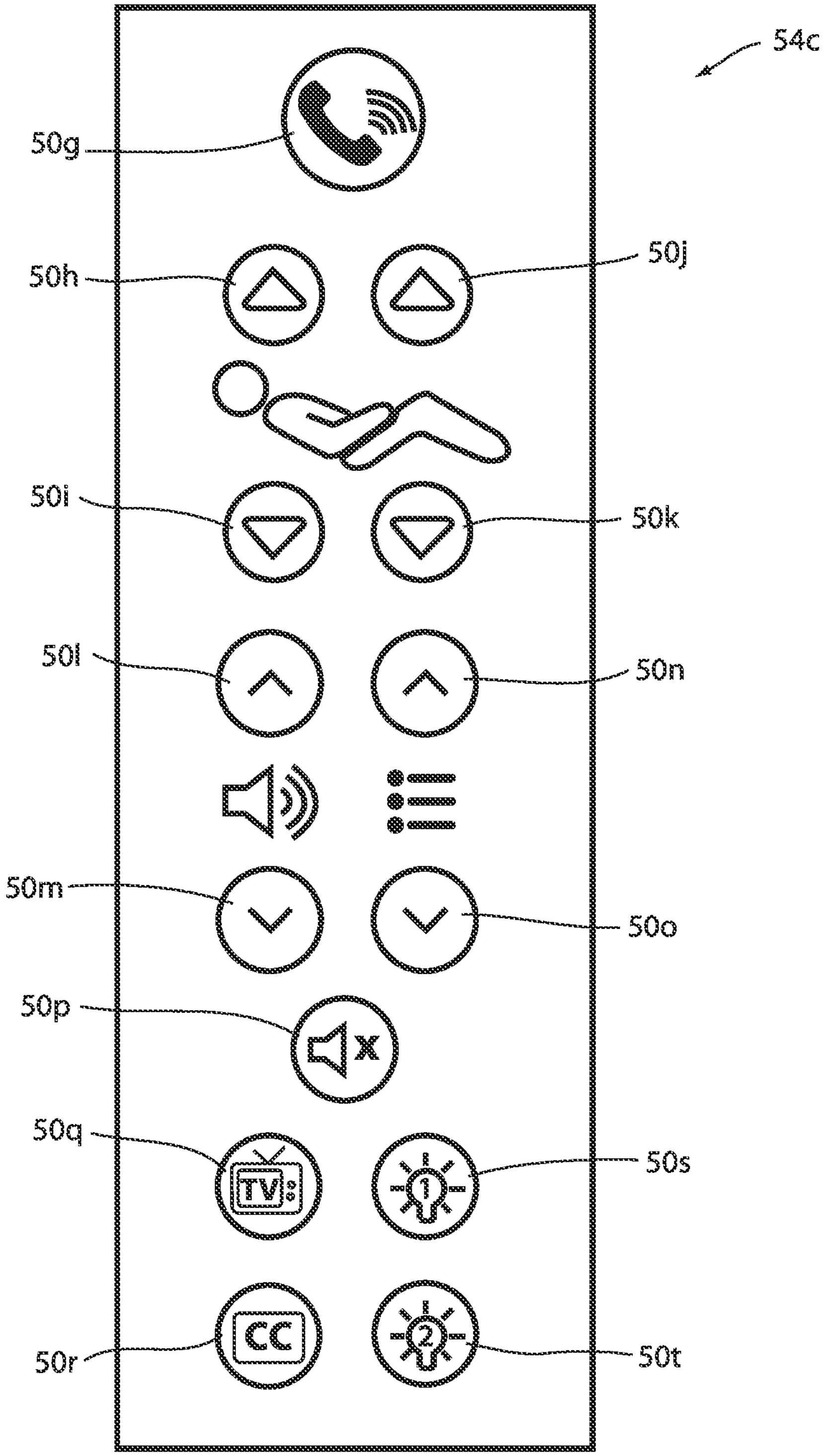
FIG. 3 is a plan view of an illustrative patient control panel of the patient support apparatus of FIG. 1.

FIG. 3 illustrates one example of a patient control panel 54*c* that may be incorporated into patient support apparatus 20 and positioned at a location on patient support apparatus 20 that is convenient for a patient to access while supported on support deck 30, such as on an interior side of one of the siderails 36. Control panel 54*c* includes a plurality of controls 50*g-t* that are intended to be operated by a patient. A nurse call control 50*g*, when pressed by the patient, sends a signal to a nurse call system requesting that a remotely positioned nurse talk to the patient. A Fowler-up control 50*h*, when pressed by the patient, causes a motorized actuator onboard patient support apparatus 20 to raise Fowler section 44 upwardly. A Fowler-down control 50*i*, when pressed by the patient, causes the motorized actuator to lower Fowler section 44 downwardly. A gatch-up control 50*j*, when pressed by the patient, causes another motorized actuator to raise a knee section of support deck 30, while a gatch-down control 50*k* causes the motorized actuator to lower the knee section of support deck 30. The knee section may refer to the joint that couples thigh section 46 to foot section 48.

A volume-up control 50*l*, when pressed by the patient, causes patient support apparatus 20 to send a signal to an in-room television instructing it to increase its volume, while a volume down control 50*m*, when pressed, causes patient support apparatus 20 to send a signal to the television instructing it to decrease its volume. A channel-up control 50*n*, when pressed by the patient, causes patient support apparatus 20 to send a signal to the television instructing it to increase the channel number, while a channel-down control 50*o*, when pressed, causes patient support apparatus 20 to send a signal to the television instructing it to decrease the channel number.

A mute control 50*p*, when pressed, causes patient support apparatus 20 to send a signal to the television instructing it to either mute itself or unmute itself, depending upon whether the television is currently muted or unmuted. In other words, mute control 50*p* is a toggle control that alternatingly sends mute and unmute commands to the television when it is pressed.

Power control 50*q* is a toggle control that, when pressed, sends a signal to the television to either turn on or turn off, depending upon the television's current power status. Closed-captioning control 50*r* is another toggle control that, when pressed, sends a signal to the television to either turn on its closed-captioning feature or to turn off its closed captioning feature, depending upon whether the closed-captioning feature is currently on or off.

Control 50*s* is a toggle control that, when pressed, sends a signal to a first light to either turn on or turn off, depending upon the current state of that first light. Control 50*t* is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54*c*, but also the functions of the controls 50 on control panel 54*c*, the layout of the controls 50 on control panel 54*c*, and/or other aspects of control panel 54*c* may be modified from what is shown in FIG. 3. In some embodiments, control panel 54*c* is implemented on a pendant controller that includes a cable that is plugged into a port on patient support apparatus 20. In other embodiments, one or more of the controls 50 of control panel 54*c* may be omitted, augmented, and/or split amongst other controls panels and/or locations. Still other manners of implementing control panel 54*c* are also possible.

Figure 4:
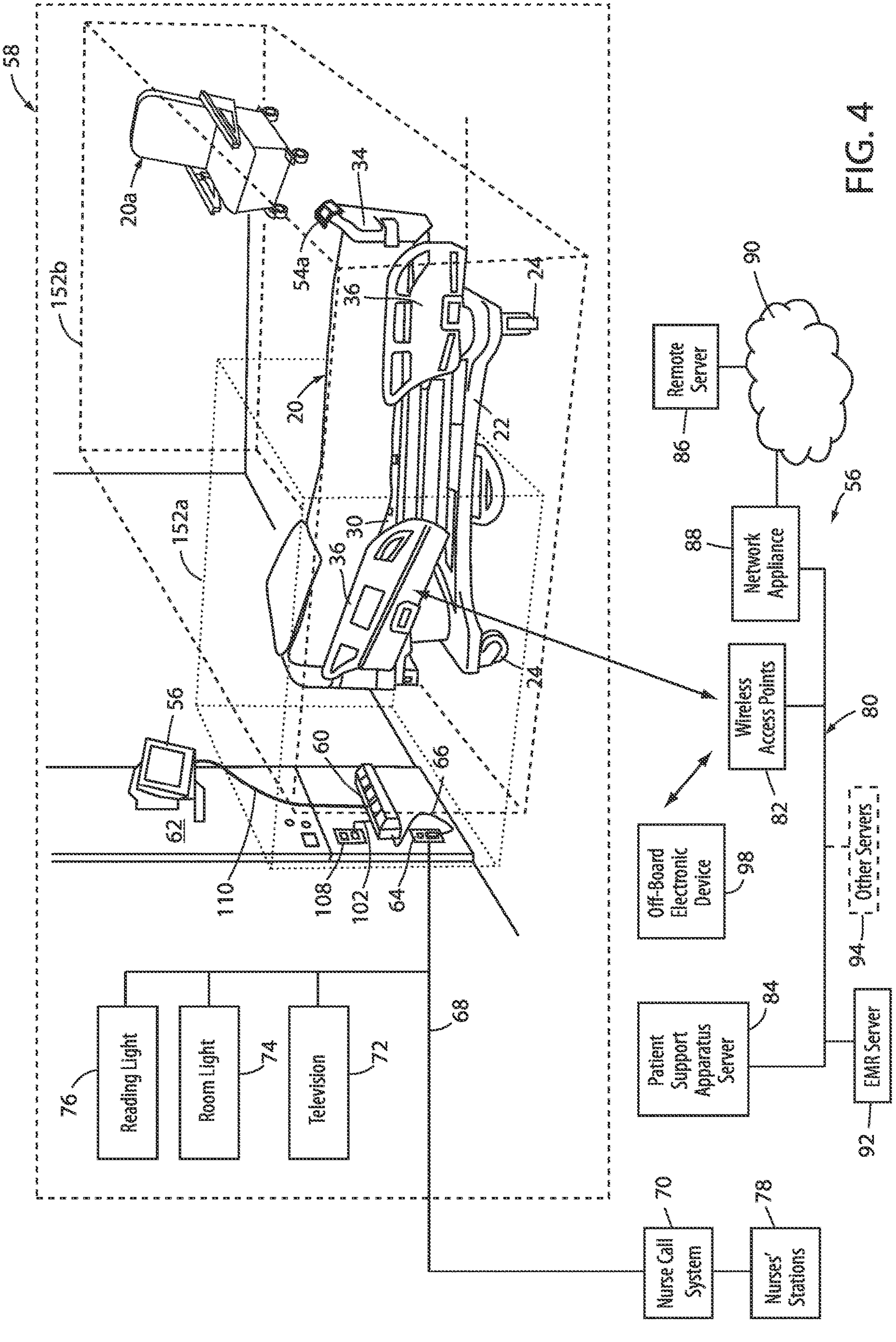
FIG. 4 is a perspective view of the patient support apparatus, a second patient support apparatus, a display device, and a locator unit that is used for automatically detecting the location of a patient support apparatus.

FIG. 4 illustrates patient support apparatus 20 positioned within a room 58 of a healthcare facility. FIG. 4 also illustrates additional items that may be present in a healthcare facility and which patient support apparatus 20 is configured to communicate with, including, but not limited to, a locator unit 60, a conventional local area network 80 of the healthcare facility, and one or more other devices used during the care of a patient, such as, but not limited to, a secondary patient support apparatus 20*a*. Locator units 60 are positioned at known and fixed locations within the healthcare facility in which patient support apparatus 20 is positioned. Locator units 60 function as fixed locators. That is, locator units 60 communicate with patient support apparatuses 20 and share information with them that allows the location of the patient support apparatuses 20 to be determined.

Figure 6:
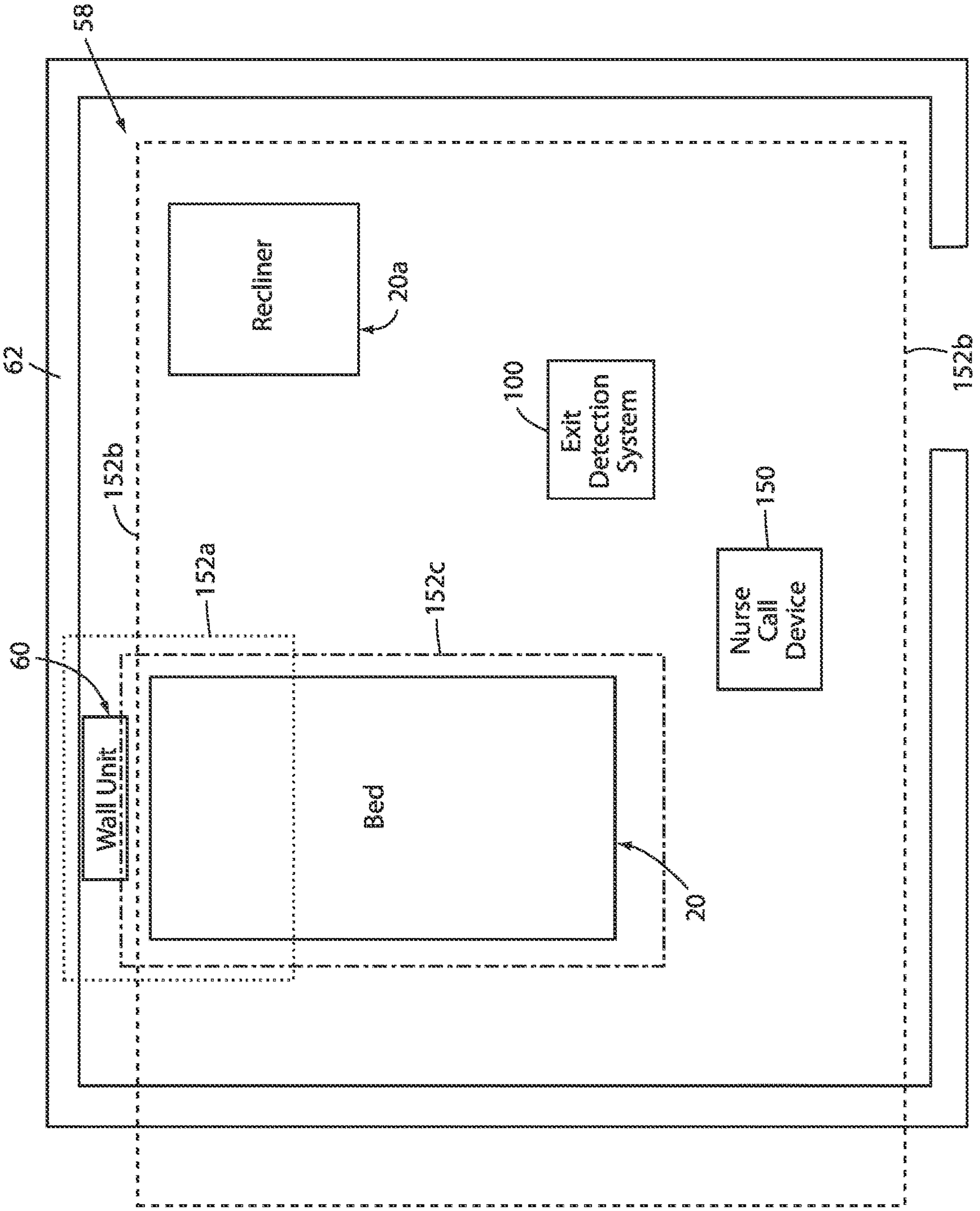
FIG. 6 is a plan view of an illustrative healthcare facility room in which is positioned a patient support apparatus, a recliner, a portable exit detection sensor, and a portable nurse call device.

In some embodiments, patient support apparatus 20 is configured to be able to communicate with at least two different types of locator units 60: linked locator units and unlinked locator units. One example of a linked locator unit 60 is shown in FIG. 4. One example of an unlinked locator unit is shown in FIG. 6 (unlinked locator unit 60*b*) of commonly assigned U.S. patent application Ser. No. 63/306,279 filed Feb. 3, 2022, by inventors Madhu Sandeep Thota et al. and entitled COMMUNICATION SYSTEM FOR PATIENT SUPPORT APPARATUSES, the complete disclosure of which is incorporated herein by reference. Patient support apparatus 20, in some embodiments, is configured to communicate with the unlinked locator units 60*b* described in the aforementioned '279 application and to perform any one or more of the functions described therein that utilize such unlinked locator units and/or information provided by such unlinked locator units.

Locator units 60 are communicatively linked to a conventional communication outlet 64 and are adapted to provide location information to patient support apparatus 20. Locator units 60 are also adapted to serve as a communication conduit for routing wireless communications between patient support apparatus 20 and one or more devices and/or systems that are communicatively coupled to communication outlet 64 (e.g. room devices 72, 74, 76, and/or nurse call system 70, FIG. 4). In general, locator units 60 are typically positioned in patient rooms of the healthcare facility where one or more communication outlets 64 are typically present. Unless explicitly stated otherwise, references herein to "locator units 60" may refer to either linked or unlinked locator units 60.

As shown in FIG. 4, locator unit 60 is adapted to be mounted to a wall 62, such as a headwall of a patient room 58 within the healthcare facility. The headwall of a conventional healthcare facility room 58 typically includes a conventional communications outlet 64 physically integrated therein. Communications outlet 64 is adapted to receive a nurse call cable 66 that physically connects at its other end either to patient support apparatus 20 (not shown) or to locator unit 60 (shown in FIG. 4). In many healthcare facilities, communication outlet 64 includes a 37-pin connector, although other types of connectors are often found in certain healthcare facilities. As will be discussed in greater detail below, locator unit 60 and nurse call cable 66 allow patient support apparatus 20 to communicate with a nurse call system, and one or more room devices positioned within room 58.

Communication outlet 64 is electrically coupled to one or more cables, wires, or other conductors 68 that electrically couple the communication outlet 64 to a nurse call system 70 and one or more conventional room devices, such as a television 72, a room light 74, and/or a reading light 76. Conductors 68 are typically located behind wall 62 and not visible. In some healthcare facilities, conductors 68 may first couple to a room interface circuit board that includes one or more conductors 68 for electrically coupling the room interface circuit board to room device 72, 74, 76 and/or nurse call system 70. Still other communicative arrangements for coupling communication outlet 64 to nurse call system 70 and/or one or more room devices 72, 74, 76 are possible.

Nurse call cable 66 (FIG. 4) enables locator unit 60 to communicate with nurse call system 70 and/or room devices 72, 74, 76, and because patient support apparatus 20 is able to wirelessly communicate with locator unit 60, patient support apparatus 20 is thereby able to communicate with nurse call system 70 and room devices 72, 74, 76. A patient supported on patient support apparatus 20 who activates a nurse call control (e.g. 50*g*; see FIG. 3) on patient support apparatus 20 causes a signal to be wirelessly sent from patient support apparatus 20 to locator unit 60, which in turn conveys the signal via nurse call cable 66 to the nurse call system 70, which forwards the signal to one or more remotely located nurses (e.g. nurses at one or more nurse's stations 78). If the patient activates one or more room device controls (e.g. controls 50*l-t*; see FIG. 3), one or more wireless signals are conveyed to locator unit 60, which in turn sends appropriate signals via nurse call cable 66 to communication outlet 64 and the room device 72, 74, 76 that change one or more features of these devices (e.g. the volume, channel, on/off state, etc.).

As is also shown in FIG. 4, patient support apparatus 20 is further configured to communicate with a local area network 80 of the healthcare facility. In the embodiment shown in FIG. 4, patient support apparatus 20 includes a wireless network transceiver 96 (FIG. 5) that communicates wirelessly with local area network 80. Network transceiver 96 is, in at least some embodiments, a WiFi transceiver (e.g. IEEE 802.11) that wirelessly communicates with one or more conventional wireless access points 82 of local area network 80. In other embodiments, network transceiver 96 may be a wireless transceiver that uses conventional 5G technology to communicate with network 80, one or more servers hosted thereon, and/or other devices. In some embodiments, network transceiver 96 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 96 is a wired transceiver that is adapted to allow patient support apparatus 20 to communicate with network 80 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 96 for communicating with network 80 via a wired connection and a wireless transceiver 96 for wirelessly communicating with network 80.

Patient support apparatus 20 is configured to communicate with one or more servers on local area network 80 of the healthcare facility. One such server is a patient support apparatus server 84. Patient support apparatus server 84 is adapted, in at least one embodiment, to receive status information from patient support apparatuses 20 positioned within the healthcare facility and distribute this status information to caregivers, other servers, and/or other software applications. As will be discussed in greater detail below, server 84 may also be configured to receive data from one or more medical devices that are positioned within one or more volumes of space defined around patient support apparatus 20 and/or within a volume of space defined around locator units 60. In some embodiments where data from medical devices is collected, the data from one or more of the medical devices may be forwarded to an Electronic Medical Records (EMR) server 92, and/or to one or more other servers 94 on network 80 (and/or one or more electronic devices 98), such as a caregiver assistance server and/or a caregiver assistance software application, as will also be discussed in greater detail below.

In some embodiments, patient support apparatus server 84 is configured to communicate at least some of the patient support apparatus status data and/or medical device data received from patient support apparatuses 20 to a remote server 86 that is positioned geographically remotely from the healthcare facility. Such communication may take place via a conventional network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

In some alternative embodiments, patient support apparatus 20 may be configured to communicate directly with one or more cloud-based servers, such as remote server 86, without utilizing patient support apparatus server 84. That is, in some embodiments, patient support apparatuses 20 may be configured to communicate directly with a remote server without relying upon any locally hosted servers (e.g. servers hosted on network 80). In one such embodiment, patient support apparatus 20 utilizes Microsoft's Azure could computing service to directly connect to one or more remote servers 86 without utilizing server 84. In some such embodiments, network appliance 88 is a router configured to support such direct connections. Still other types of direct-to-cloud connections may be utilized with one or more of patient support apparatuses 20. When patient support apparatus 20 is configured to directly communicate with remote server 86, patient support apparatus server 84 may be omitted and any one or more of the functions of patient support apparatus server 84 described herein may be performed by remote server 86.

Patient support apparatus server 84 is also configured to determine the location of each patient support apparatus 20 (and/or its associated devices), or receive the location of each patient support apparatus 20 (and/or its associated devices) from the patient support apparatuses 20. In some embodiments, patient support apparatus server 84 determines the room number and/or bay area of each patient support apparatus 20 and its associated devices that are positioned within a room 58, as well as the location of patient support apparatuses 20 and their associated devices that are positioned outside of a room 58, such as, those that may be positioned in a hallway, a maintenance area, or some other area. In general, patient support apparatus server 84 may be configured to determine the position of any patient support apparatus 20 that is positioned within communication range of one or more locator units 60, as well as the location of any associated devices that are positioned within one or volumes of space defined around the patient support apparatus 20, as will be discussed in greater detail below.

Patient support apparatus server 84 is adapted to communicate with EMR server 92 in order to exchange data therewith. In some embodiments, server 84 communicates with EMR server 92 in order to transmit patient data that is to be recorded in a patient's health record (e.g. vital sign readings from one or more vital sign sensors; weight readings taken from the scales built into patient support apparatuses 20; therapies provided to patients using a powered mattress 42 onboard patient support apparatuses 20; data from other devices that are determined to be associated with the patient assigned to patient support apparatus 20, etc.). In addition, server 84 communicates with EMR server 92, in some embodiments, in order to receive data from one or more of the devices that are being used with a particular patient.

It will be understood that the architecture and content of local area network 80 will vary from healthcare facility to healthcare facility, and that the example shown in FIG. 4 is merely one example of the type of network a healthcare facility may be employ. Typically, one or more additional servers 94 will be hosted on network 80 and one or more of them may be adapted to communicate with patient support apparatus server 84. Local area network 80 will also typically allow one or more electronic devices 98 to access the local area network 80 via wireless access points 82. Such electronic devices 98 include, but are not limited to, smart phones, tablet computers, portable laptops, desktop computers, smart televisions, and other types of electronic devices that include a WiFi capability and that are provided with the proper credentials (e.g. SSID, password, etc.) to access network 80 (and, in at least some situations, patient support apparatus server 84). As will be discussed in further detail herein, patient support apparatus server 84 is configured, in some embodiments, to share data with one or more electronic devices 98 that relates to patient support apparatus 20, that relates to one or more devices that are associated with patient support apparatus 20 (or the patient assigned thereto), and/or that relates to one or more medical records of the patient stored in EMR server 92.

Locator units 60 are adapted to wirelessly receive signals from patient support apparatus 20 and deliver the signals to communications outlet 64 in a manner that matches the way the signals would otherwise be delivered to communications outlet 64 if a conventional nurse call cable 66 were connected directly between patient support apparatus 20 (via a cable port 148; FIG. 5) and communications outlet 64. Locator units 60 are also adapted to transmit signals received from communications outlet 64 to patient support apparatus 20 via a BT transceiver 106 and/or a UWB transceiver 104 (FIG. 5). Thus, patient support apparatus 20 and locator unit 60 cooperate to send signals to, and receive signals from, communications outlet 64 in a manner that is transparent to communications outlet 64 such that outlet 64 cannot detect whether it is in communication with patient support apparatus 20 via a wired connection or it is in communication with patient support apparatus 20 via a wireless connection between patient support apparatus 20 and locator unit 60 (the latter of which is in wired communication with outlet 64). In this manner, a healthcare facility can utilize the wireless communication abilities of one or more patient support apparatuses 20 without having to make any changes to their existing communication outlets 64.

As noted, in addition to sending signals received from patient support apparatus 20 to communications outlet 64, locator units 60 are also adapted to forward signals received from communications outlet 64 to patient support apparatus 20. Locator units 60 are therefore adapted to provide bidirectional communication between patient support apparatus 20 and communications outlet 64. This bidirectional communication includes, but is not limited to, communicating command signals from any of controls 50 and/or from any of electronic devices 98 to corresponding room devices 72, 74, and/or 76 and communicating audio signals between a person supported on patient support apparatus 20 and a caregiver positioned remotely from patient support apparatus 20. The audio signals received by locator units 60 from a microphone on patient support apparatus 20 are forwarded to communications outlet 64 (for forwarding to nurse call system 70), and the audio signals of a remotely positioned nurse that are received at communications outlet 64 (from nurse call system 70) are forwarded to a speaker onboard patient support apparatus 20.

Nurse call cable 66, in some embodiments, includes a conventional 37 pin connector on each end, one of which is adapted to be inserted into outlet 64 and the other one of which is adapted to be inserted into locator unit 60. Such 37 pin connections are one of the most common types of connectors found on existing walls of medical facilities for making connections to the nurse call system 70 and room devices 72, 74, and 76. Locator unit 60 and nurse call cable 66 are therefore configured to mate with one of the most common type of communication outlets 64 used in medical facilities. Such 37 pin connectors, however, are not the only type of connectors, and it will be understood that locator units 60 can utilize different types of connectors that are adapted to electrically couple to different types of nurse call cables 66 and/or different types of communication outlets 64. One example of such an alternative communications outlet 64 and cable 66 is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors may be utilized.

Locator unit 60 (FIG. 4) also includes an electrical cord 102 having a plug positioned at a far end that is adapted to be inserted into a conventional electrical outlet 108. Electrical cord 102 enables locator unit 60 to receive power from the mains electrical supply via outlet 108. It will be appreciated that, in some embodiments, locator unit 60 is battery operated and cord 102 may be omitted. In still other embodiments, locator unit 60 may be both battery operated and include cord 102 so that in the event of a power failure, battery power supplies power to locator unit 60, and/or in the event of a battery failure, electrical power is received through outlet 108.

In some embodiments, locator units 60 include a video port 120 that is adapted to receive a display cable 110 (FIG. 4). The display cable 110 is adapted to couple to locator unit 60 at one end and a display device 56 at its opposite send. Locator unit 60 may be configured to use cable 110 to send data to display device 56 that is to be displayed thereon. Such data may include data from one or more medical devices (or other types of devices) that are associated with the patient on patient support apparatus 20 (or with patient support apparatus 20 itself), status data from one or more sensors onboard patient support apparatus 20, location data regarding the location of patient support apparatus 20, and/or other data. Cable 110 may be a High-Definition Multimedia Interface (HDMI) cable, a Video Graphics Array (VGA) cable, a DisplayPort (DP) cable, a plurality of Radio Corporation of America (RCA) cables, a Digital Visual Interface (DVI) cable, and/or another type of cable. Locator unit 60 is configured to include a complementary type of connector that mates with a connector on an end of cable 110. Further details regarding the communication between patient support apparatus 20 and display device 56 are provided below and, in some embodiments, patient support apparatus 20 may be configured to communicate directly with certain display devices without using locator unit 60 as a communication intermediary.

In addition to any of the structures and functions described herein, locator units 60 are configured to communicate location data to patient support apparatus 20 that enables patient support apparatus 20 and/or patient support apparatus server 84 to determine the location of patient support apparatus 20 within the healthcare facility. In general, such location determination is carried out by patient support apparatus 20 analyzing wireless signals communicated between itself and locator unit 60 in order to determine its position relative to locator unit 60. If patient support apparatus 20, or a predefined reference point on patient support apparatus 20 (e.g. its head end) is positioned within a threshold distance of locator unit 60, patient support apparatus 20 associates itself with the locator unit 60. When associated, patient support apparatus 20 communicates data to locator unit 60, receives data from locator unit 60, and also deems its location within the healthcare facility to be the same as location of locator unit 60. When patient support apparatus 20 is outside of the threshold distance, it does not associate itself with locator unit 60, and therefore does not exchange data with locator unit 60 or consider its location to be the same as that of locator unit 60's location.

In some embodiments, patient support apparatus 20 is configured to associate itself with a particular locator unit 60 if both the patient support apparatus 20 (or a reference point thereon) and locator unit 60 are concurrently positioned within a common volume of space **152*a* (FIG. 4). In some embodiments, the volume of space 152*a* is defined with respect to each locator unit 60 and does not move. In other embodiments, the volume of space 152*a* is defined with respect to patient support apparatus 20 and moves as patient support apparatus 20 moves. In both embodiments, patient support apparatus 20 associates itself with a nearby locator unit 60 if both the locator unit 60 and the patient support apparatus 20 (or a reference point thereon) are concurrently within the predefined volume of space 152***a*. An example of this is shown in FIG. 4, where head end 38 of patient support apparatus 20 and locator unit 60 are both positioned inside of volume of space 152*a*, and patient support apparatus 20 has therefore associated itself with that particular locator unit 60.

After associating itself with a particular locator unit 60, patient support apparatus 20 is configured to be able to have its absolute position within the healthcare facility determined by receiving a unique locator identifier (ID) 122 (FIG. 5) from the locator unit 60. The location of each locator unit 60 in the healthcare facility is surveyed during the installation of locator units 60, and the unique IDs 122 of each locator unit 60 are also recorded during the installation of locator units 60. This surveying information and corresponding ID information may be stored in patient support apparatus server 84 and/or onboard patient support apparatus 20, thereby enabling patient support apparatus 20 and/or patient support apparatus server 84 to determine the location of a patient support apparatus 20 once it is associated with a particular locator unit 60.

In those embodiments where patient support apparatus server 84 is configured to determine the location of patient support apparatus 20, patient support apparatus 20 sends its relative position information and/or the ID 122 of the associated locator unit 60 (and its own unique patient support apparatus ID 130 (FIG. 5) to server 84. Server 84 includes a table of all of the locations of the locator units 60 (which, as noted, is generated via a surveying operation during the installation of locator units 60), and it uses that table to correlate the patient support apparatus IDs 130 and the locator unit IDs 122 it receives to specific locations within the healthcare facility. Thus, if a particular patient support apparatus 20 (with a particular ID 130) sends an associated locator unit ID 122 that corresponds to room 430, server 84 determines that that particular patient support apparatus 20 is currently located in room 430. Generally speaking, and as will be discussed in greater detail below, the location of a patient support apparatus 20 is deemed to correspond to whichever locator unit 60 it is currently associated with, and if it is not currently associated with any locator unit 60, its location may be considered to be indeterminate.

In some embodiments of patient support apparatus 20 and locator unit 60, the relative location of patient support apparatus 20 to a locator unit 60 is determined solely using ultra-wideband communication between the patient support apparatus 20 and the locator unit 60. Alternatively, in some embodiments, patient support apparatus 20 solely uses short range infrared communications with locator unit 60 to determine its relative location, wherein such short range infrared communications are only possible when the patient support apparatus 20 is positioned within a close proximity to the locator unit 60 (e.g. in the range of about 1-3 unobstructed meters). In these latter embodiments, patient support apparatus 20 may report that its location coincides with that of the nearby locator unit 60 when it is able to successfully communicate with the nearby locator unit 60 using these short range infrared communications. Still further, in some embodiments, patient support apparatus 20 and locator unit 60 may communicate with each other using both infrared and ultra-wideband communications. Further details regarding the use of short range infrared communications for location determination are described in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

In some embodiments, locator units 60 and/or patient support apparatuses 20 may be constructed to include any or all of the functionality of the wireless headwall units and/or patient support apparatuses disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; in commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION; and/or in commonly assigned U.S. patent application Ser. No. 63/245,245 filed Sep. 17, 2021, by inventors Kirby Neihouser et al. and entitled SYSTEM FOR LOCATING PATIENT SUPPORT APPARATUSES, the complete disclosures of all of which are incorporated herein by reference.

Still further, in some embodiments, locator units 60 and/or patient support apparatuses 20 may be constructed to include any of the features and/or functions of the headwall units 144*a* and/or patient support apparatuses disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

FIG. 5 depicts a block diagram of patient support apparatus 20, a locator unit 60, an exit detection sensor 100, a nurse call device 150, a display device 56, a secondary patient support apparatus 20*a*, and network 80. As will be discussed in greater detail below, patient support apparatus 20 is configured to automatically determine the location of one or more secondary patient support apparatuses 20*a*, locator units 60, exit detection sensors 100, nurse call devices 150, and/or other devices. In addition, patient support apparatus 20 is configured to automatically carry out communications with those devices if they are positioned within a defined proximity to patient support apparatus 20. In some embodiments, if a particular device is positioned within the defined proximity, patient support apparatus 20 automatically associates the device with the patient assigned to patient support apparatus 20 (and/or with patient support apparatus 20 itself), and causes data from that device (or devices) to be displayed on one or more of display devices 56, and/or forwards data from that device (or devices) to patient support apparatus server 84 and/or EMR server 92 in communication with network 80. When the device is positioned outside the defined proximity, patient support apparatus 20 may automatically disassociate itself from the device and, in some situations, terminate communications with the device and/or inform patient support apparatus server 84 of the disassociation.

Locator unit 60 includes an ultra-wideband transceiver 104, a Bluetooth transceiver 106, a locator unit controller 112, configuration circuitry 114, a television controller 116, a headwall interface 118, a video port 120, a unit ID 122, and, in some embodiments, an infrared transceiver 124. Bluetooth transceiver 106 is adapted to communicate with a Bluetooth transceiver 128 onboard patient support apparatus 20 using RF waves in accordance with conventional Bluetooth standards (e.g. IEEE 802.14.1 and/or any of the standards maintained by the Bluetooth Special Interest Group (SIG) of Kirkland, Washington, USA). In some embodiments, transceivers 106 and 128 utilize Bluetooth Low Energy communications.

Ultra-wideband transceiver 104 is adapted to communicate with one or more ultra-wideband transceivers 132 positioned onboard patient support apparatus 20. Transceiver 104 is adapted to determine a distance between itself and patient support apparatus 20. Alternatively, or additionally, transceiver 104 may be adapted to allow one or more of the UWB transceivers 132 onboard patient support apparatus 20 to determine their distance(s) from transceiver 104. In some embodiments, transceivers 104 and 132 use time of flight (TOF) computations to determine these distances. In other embodiments, transceivers 104 and 132 may utilize other techniques for determining their distances from each other, either in addition to, or in lieu of, TOF computations. In some embodiments, transceivers 104, 132 may also determine an angle between themselves using angular information derived from antenna arrays positions onboard transceivers 104, 132, or by using other techniques. The position and orientation of each transceiver 132 onboard patient support apparatus 20 is known and stored in an onboard memory 134 and used to determine the position and orientation of patient support apparatus 20 with respect to the locator unit(s) 60 with which it is communicating.

In some embodiments, transceivers 104, 132 are implemented as any of the Trimension™ ultra-wideband modules available from NXP Semiconductors of Austin, Texas. These modules include, but are not limited to, the Trimension™ UWB modules ASMOP1BO0N1, ASMOP1CO0R1, and/or the ASMOP1CO0A1, that utilize any of the following chips: the NXP SR150, SR100T, SR040, NCJ29D5, and/or the OL23DO chips. Modules manufactured and/or marketed by other companies may also be used, including, but not limited to, the Decawave DWM1000, DWM10001C, DWM3000 modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB modules may be used to implement transceivers 104 and 132.

Locator unit controller 112 is adapted to control the operation of transceivers 104, 106, configuration circuitry 114, TV controller 116, headwall interface 118, video port 120, and, if included, IR transceiver 124 (FIG. 5). When infrared transceiver 124 is included, it may be included to provide backwards compatibility to patient support apparatuses 20 that are not equipped with a UWB transceiver 132. That is, some healthcare facilities may include one or more patient support apparatuses that are not equipped with a UWB transceiver 132, but that do include an IR transceiver that is adapted to communicate with IR transceiver 124. When locator unit 60 includes IR transceiver 124, it is able to communicate its unit ID 122 to such patient support apparatuses via IR transceiver 124, which is a short range transceiver that is configured to only communicate with an adjacent patient support apparatus when the patient support apparatus is nearby (e.g. without about five feet or so). Such an adjacent patient support apparatus 20 then communicates the received locator unit ID 122 along with its own unique ID 130 (FIG. 5) to server 84 which, as noted previously, is able to correlate the locator unit ID 122 to a particular location with the healthcare facility. In this manner, server 84 is able to use locator units 60 determine the location of versions of patient support apparatuses 20 that don't have a UWB transceiver 132, but that do have an IR transceiver.

Headwall interface 118 is adapted to change the electrical state of one or more pins that are in electrical communication with communication outlet 64 (via cable 66). Headwall interface 118 changes these electrical states in response to instructions from controller 112. For example, if the exit detection system 136 of patient support apparatus 20 detects a patient exit, a controller 140 of patient support apparatus 20 sends an exit alert signal to locator unit 60 and controller 112 responds by instructing headwall interface 118 to change the electrical state of at least one pin that is used to signal an exit alert (or a generic priority alert) to the nurse call system 70 via communications outlet 64. Additionally, if an exit detection sensor 100 associated with patient support apparatus 20 detects an exit from a secondary patient support apparatus 20*a*, the exit detection sensor 100 may transmit an exit detection alert signal to patient support apparatus 20, which in turn forwards the exit alert signal to locator unit 60, and controller 112 responds by instructing headwall interface 118 to change the electrical state of the same pin or pins that it does in response to receiving an exit detection alert from exit detection system 136, as will be discussed in greater detail below.

In some embodiments, headwall interface 118 may be constructed in the same manner as, and/or may include any one or of the functions as, the cable interface 88 described in commonly assigned U.S. patent application Ser. No. 63/193,778 filed May 27, 2021, by inventors Krishna Bhimavarapu et al. and entitled PATIENT SUPPORT APPARATUS AND HEADWALL UNIT SYNCING, the complete disclosure of which is incorporated herein by reference. Alternatively, or additionally, headwall interface 118 may be constructed in the same manner as, and/or may include any one or more of the same functions as, the headwall interface 120 disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference. Locator unit 60 may also be configured to perform any of the functions of the headwall units 94 disclosed in the above-mentioned '778 patent application.

Configuration circuitry 114 and TV controller 116 may be configured to perform any of the same functions as, and/or be constructed in any of the same manners as, the configuration circuitry 132 and the TV control circuit 134, respectively, of commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which has already been incorporated herein by reference. Additionally, or alternatively, locator unit 60 may be configured to perform any of the functions of the headwall units 144 disclosed in the aforementioned '508 patent application.

Patient support apparatus 20 includes a controller 140, a memory 134, exit detection system 136, a microphone 142, Bluetooth transceiver 128, one or more UWB transceivers 132, display 52 (which may be part of control panel 54*a*, and/or another control panel 54), network transceiver 96, a near field transceiver 144, a nurse call interface 146, and a plurality of additional components that are not shown in FIG. 5. Each UWB transceiver 132 is positioned at a known location on patient support apparatus 20. This known location information is stored in memory 134 and/or elsewhere, and may be defined with respect to any suitable frame of reference that is common to patient support apparatus 20. The known location information may include the spatial relationship between UWB transceivers 132 and/or any other components of patient support apparatus 20. For example, in some embodiments, the known location information includes the spatial relationship not only between UWB transceivers 132, but also the spatial relationships between UWB transceivers 132 and one or more of the following: the head end 38 of patient support apparatus 20, the foot end of patient support apparatus 20, the sides of patient support apparatus 20, a reference point defined on patient support apparatus 20, the floor, and/or other components and/or landmarks of patient support apparatus 20. In some embodiments, this location information is used to determine the orientation of patient support apparatus 20 with respect to one or more walls 62, locator units 60, another patient support apparatus 20*a*, and/or another object or structure within the healthcare facility.

In some embodiments, patient support apparatus 20 includes four UWB transceiver 132, each of which are position generally adjacent one of the four corners of patient support apparatus 20. In some such embodiments, the four UWB transceiver 132 are attached to, or positioned near, the four corners of litter frame 28. In other embodiments, the four UWB transceivers 132 are attached to, or positioned near, the four corners of base 22. In some embodiments, each of the four UWB transceivers 132 are attached to the corners of support deck 30. Still other locations of the UWB transceivers 132, as well as different numbers of the UWB transceiver 132, may be incorporated into patient support apparatus 20. In those embodiments of patient support apparatus 20 where one or more of the UWB transceiver 132 are coupled to components of patient support apparatus 20 that are movable (e.g. litter frame 28, which can have its height and orientation changed; or support deck 30 that can have its sections, such as head section 44, pivoted), sensors are included within patient support apparatus 20 that communicate the current position of the movable component to controller 140 so that controller 140 is able to determine the current positions of the UWB transceivers 132 and use those positions when determining the current location of a device, such as a secondary patient support apparatus 20*a*, a nurse call device 150, an exit detection sensor 100, a locator unit 60, and/or another device.

Controller 140, as well as controller 112, may take on a variety of different forms. In the illustrated embodiment, each of these controllers is implemented as a conventional microcontroller. However, these controllers may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 112 and 140 when carrying out the functions described herein, as well as the data necessary for carrying out these functions, are stored in a corresponding memory that is accessible to that particular controller (e.g. memory 134 for controller 140, and a memory (not shown) for controller 112). In some embodiments, controller 140 may include and/or work with a microcontroller that is integrated into, or associated with, UWB transceiver(s) 132, and controller 112 may include and/or work with a microcontroller that is integrated into, or associated with, UWB transceiver 104.

Controller 140 utilizes UWB transceivers 132 to determine the relative position of patient support apparatus 20 with respect to one or more nearby locator units 60 and to determine the relative position of one or more objects or devices with respect to patient support apparatus 20. If patient support apparatus 20 is positioned within range of a locator unit 60, its UWB transceivers 132 communicate with the UWB transceiver 104 positioned on that locator unit 60, and the transceivers 132 and 104 exchange signals that enable them to determine the distances between themselves. This distance determination is done for each UWB transceiver 132 positioned onboard patient support apparatus 20 (or for as many as is necessary in order to determine an accurate position of locator unit 60 relative to patient support apparatus 20).

In some embodiments, UWB transceivers 104, 132 may also be configured to determine an angular relationships between themselves. The distance (and angle information) in at least some embodiments is calculated by UWB transceiver 132 and controller 140 of patient support apparatus 20. In other embodiments, UWB transceiver 104 and controller 112 may calculate the distance (and angle information) and forward the results of this calculation to patient support apparatus 20 (either via UWB transceiver 104 or BT transceiver 106). In either situation, patient support apparatus controller 140 is informed of the distances (and, in some embodiments, as noted, the angle information) between transceivers 132 and 104. These distances and orientations are then used to calculate a relative position of patient support apparatus 20 to the locator unit 60 in a common frame of reference that may be defined in a fixed relationship to the patient support apparatus 20 or in a fixed relationship to the locator unit 60.

Although FIGS. 4 and 5 only illustrate a single locator unit 60, it will be understood that a typical healthcare facility will include multiple locator units 60 positioned at different locations throughout the facility, including ones positioned within patient rooms and others positioned outside of patient rooms. Typically, at least one locator unit 60 will be positioned in each patient room of the healthcare facility, and if the patient room is intended to be occupied by more than one patient (e.g. it includes multiple bays), then additional locator units 60 may be included so that each patient support apparatus 20 will have a locator unit 60 positioned adjacent to each bay area in the room. Additional locator units 60, such as unlinked locator units 60, may also be positioned at other locations through the healthcare facility.

The location of patient support apparatus 20 relative to locator units 60 is repetitively determined by an exchange of communication signals between UWB transceivers 104 and 132. This exchange is initiated by an interrogation signal that may be sent by the UWB transceivers 104 of the locator unit 60, and/or it may be sent by the UWB transceivers 132 of the patient support apparatuses 20. The trigger for sending these interrogation signals (from either source) may simply be the passage of a predefined interval of time, in at least some embodiments. That is, in some embodiments, patient support apparatus 20 and/or locator units 60 may be configured to periodically send out an interrogation signal that will be responded to by any UWB transceivers 104 or 132 that are positioned with range of that signal. In those embodiments where patient support apparatuses 20 are configured to send out such an interrogation signal, the time intervals between the interrogation signals may be varied depending upon the location and/or other status of the patient support apparatus 20. For example, in some embodiments, patient support apparatuses 20 may be configured to send out the interrogation signals with longer timer intervals between them when the patient support apparatus is stationary, and to send out the interrogation signals with shorter time intervals between them when the patient support apparatus 20 is in motion. Indeed, in some embodiments, after patient support apparatus 20 has ceased moving, controller 140 may be configured to cease sending out such interrogation signals until it once again starts moving. In any of the aforementioned embodiments, motion of the patient support apparatus 20 may be detected in any suitable manner, such as by including one or more motion sensors on the patient support apparatus 20 (e.g. one or more accelerometers), and/or by monitoring the values of the repetitive distance measurements and looking for changes indicative of movement.

The measured distances (and/or angular information between locator units 60 and patient support apparatuses 20) that are generated from the communications between UWB transceivers 104, 132 may utilize Angle of Arrival (AoA) information, Time of Flight (TOF) information, Channel State Information, Time Difference of Arrival (TDoA) information, Two-Way Ranging (TWR) ranging information, and/or other information. In some embodiments, each transceiver 104, 132 includes an array of antennas that are used to generate distance and/or angular information with respect to the transceivers 104, 132 in which it is in communication. Still further, in some embodiments, UWB transceivers 104, 132 include one or more of their own microcontrollers, and the location of UWB transceivers 104, 132 may be determined by these internal microcontrollers without utilizing controller 140 and/or 112. In other embodiments, controllers 112 and/or 140 may work in conjunction with the microcontrollers of transceivers 104, 132 to determine their relative locations to each other.

Nurse call interface 146 of patient support apparatus 20 (FIG. 5) includes Bluetooth transceiver 128 and a cable port 148, in some embodiments. Nurse call interface 146 provides an interface for patient support apparatus 20 to communicate with outlet 64 of nurse call system 70. That is, nurse call interface 146 provides the means for patient support apparatus 20 to bidirectionally communicate with communication outlet 64. As has been discussed, in some situations, patient support apparatus 20 uses Bluetooth transceiver 128 to communicate with Bluetooth transceiver 106 of locator unit 60, and locator unit 60 forwards communications back and forth between outlet 64 and patient support apparatus 20. In other words, in some situations, locator unit 60 functions as an intermediary between nurse call interface 146 and outlet 64. Alternatively, a nurse call cable 66 may be directly coupled between patient support apparatus 20 and wall outlet 64, thereby avoiding the need to use locator unit 60 as a communication intermediary. In such situations, one end of a nurse call cable 66 is plugged into cable port 148 of patient support apparatus 20 and the other end of the cable 66 is plugged directly into outlet 64. Nurse call interface 146 thereby provides patient support apparatus 20 with the ability to communicate either wirelessly or via wired means with the outlet 64.

Patient support apparatus 20 also includes, in at least some embodiments, a microphone 142 (FIG. 5) that is used to detect the voice of the patient when the patient wants to speak to a remotely positioned nurse. The patient's voice is converted to audio signals by microphone 142 and controller 140 is adapted to forward these audio signals to an adjacent communications outlet 64 positioned in wall 62 (FIG. 4). When a cable 66 is coupled between cable port 148 of patient support apparatus 20 and outlet 64, controller 140 forwards these audio signals to outlet 64 via the cable 66. When no such cable 66 extends between patient support apparatus 20 and outlet 64, controller 140 wirelessly forwards these audio signals to the locator unit 60 that it is currently associated with (using transceiver 128, or in some embodiments, one of transceivers 132) and controller 112 of locator unit 60 forwards these audio signals to outlet 64. As was noted, outlet 64 is in electrical communication with a conventional nurse call system 70 that is adapted to route the audio signals to the correct nurse's station 78, and/or other location. In some embodiments, microphone 142 acts as both a microphone and a speaker. In other embodiments, a separate speaker may be included in order to communicate the voice signals received from the remotely positioned nurse. In some embodiments, the audio communication between patient support apparatus 20 and communications outlet 64 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

After the installation of locator units 60 in a particular healthcare facility, the location of each locator unit 60 within that facility is recorded. In some embodiments, the coordinates of the locations of locator units 60 are recorded in a common frame of reference (or converted to a common frame of reference after recordation). Such coordinates may be three dimensional (i.e. include a vertical and two horizontal components), or they may be two dimensional (no height component). In other embodiments, a more generalized location of one or more locator units 60 is determined, rather than the precise coordinates of the locator units 60. The generalized location of the locator units 60 may include an indication of the room, bay, area, hallway, portion of a hallway, wing, maintenance area, etc. that the locator unit 60 is positioned in. In still other embodiments, the locations of one or more locator units 60 are determined both generally and more precisely.

Regardless of how the location of each locator unit 60 is initially determined after they are installed in a healthcare facility (e.g. whether their coordinates are determined or a more generalized location is determined), the locations of all of the locator units 60, as well as their unique IDs 122, are stored in a memory accessible to server 84. Server 84 then uses this location data and ID data to determine the location of a patient support apparatus 20. Alternatively, or additionally, the location data and ID's 122 are forwarded to patient support apparatuses 20 for storage in their onboard memories 134 and for use in determining their own locations. In some embodiments, the location of each locator unit 60 (whether specific and/or general) may also, or alternatively, be stored in a memory within that particular locator unit 60 and shared with the devices it communicates with (e.g. patient support apparatuses 20). In some other embodiments, the location of each locator unit 60 may be stored in multiple locations.

It will be appreciated that patient support apparatuses 20 are configured to communicate with locator units 60 regardless of the orientation of the patient support apparatus 20.

That is, the UWB transceivers 104 and 132 are radio frequency transceivers that do not rely on line of sight communication, unlike the IR transceiver 124 (if present). Thus, the patient support apparatuses 20 do not have to be pointed in any particular direction with respect to the locator units in order for transceivers 104 and 132 to communicate. This differs from some prior art systems that use IR communication between the patient support apparatuses 20 and the locator units and that require the IR transceiver onboard the patient support apparatus to be aimed toward the locator unit in order for communication to be established. It will also be understood that locator units 60 can be positioned on walls, columns, ceilings, or any other fixed structures within the healthcare facility.

Patient support apparatus 20 is also configured to use UWB transceivers 132 to determine the position of various other devices relative to patient support apparatus 20, such as one or more exit detection sensors 100, one or more nurse call devices 150, one or more secondary patient support apparatuses 20*a*, and/or one or more other devices that are physically separated from patient support apparatuses 20 (FIG. 5). As will be discussed in greater detail below, controller 140 uses UWB transceivers 132 to determine the relative position of these devices by communicating with one or more respective UWB transceivers that are either built into those devices or attached to a tag that is affixed to those devices. Such UWB transceivers operate in the same manner as UWB transceivers 132 and/or UWB transceiver 104 of locator units 60. And, as will also be discussed in greater detail below, controller 140 of patient support apparatus 20 uses the relative position information to determine how it will interact with these devices, including whether to associate with these devices or not. When controller 140 associates patient support apparatus 20 with one or more of these devices, as will be discussed in greater detail below, controller 140 and/or server 84 may take one or more of the following actions: display data from these devices on display 52 and/or display device 56, send data from one or more of these devices to patient support apparatus server 84 and/or EMR server 92 via network transceiver 96, send one or more signals from these devices to communication outlet 64 (via a cable 66 or through locator unit 60), forward one or more signals from outlet 64 to one or more of these devices, retrieve data from EMR server 92 that was generated by these devices, retrieve data from these devices via another route that is independent from EMR server 92, and/or take other actions.

Nurse call device 150 (FIG. 5) includes a UWB transceiver 154, a controller 156, a near field transceiver 158, a nurse call button 160, a unique ID 166, and—in some embodiments, a microphone/speaker 162 and a Bluetooth transceiver 164. UWB transceiver 154 is adapted to communicate with the UWB transceivers 132 positioned onboard patient support apparatus 20 so that the position of nurse call device 150 relative to patient support apparatus 20 can be repetitively determined. UWB transceiver 154 may be the same as all of the other UWB transceivers discussed herein (e.g. UWB transceivers 132, 104, etc.). UWB transceiver 154 is further adapted to transmit the unique ID 166 of nurse call device 150 to patient support apparatus 20 so that patient support apparatus 20 knows which specific nurse call device 150 it is communicating with.

Controller 156 of nurse call device 150 is adapted to oversee the operation of nurse call device 150, process the communications of UWB transceiver 154 with other UWB transceivers (e.g. transceivers 132), respond to the activation of nurse call button 160, and, when included, oversee the operation of microphone/speaker 162 and Bluetooth transceiver 164. Nurse call device 150 is designed to be standalone device that can be attached to a structure within a patient's room and give that structure a nurse call ability (i.e. the ability for an adjacent patient to utilize nurse call device 150 to summon a nurse). For example, a secondary patient support apparatus 20*a*, such as a recliner, chair, or other patient support, may be constructed by its manufacturer without the ability of a patient to use it to summon a nurse. By physically attaching nurse call device 150 to the secondary patient support apparatus 20*a*, the secondary patient support apparatus 20*a* then obtains the ability for the patient to summon a nurse, as will be discussed in greater detail below.

When controller 156 detects that nurse call button 160 is pressed, it transmits a nurse call signal to patient support apparatus 20, using either UWB transceiver 154 and/or Bluetooth transceiver. Controller 140 of patient support apparatus 20 is configured to respond to this nurse call signal in the same manner as it reacts to the activation of nurse call control 50*g* (FIG. 3) on one of its control panels 54. Control 50*g*, as was described previously, causes controller 140 to send a signal to nurse call system 70 requesting that a remotely positioned nurse talk to the patient. More specifically, controller 140 responds to both the activation of control 50*g* and the receipt of a nurse call button press from nurse call device 150 by changing an electrical characteristic of one or more of the pins within communication outlet 64. If patient support apparatus 20 is coupled to outlet 64 by cable 66, controller 140 changes the state of one or more relays onboard patient support apparatus 20 that are in electrical communication with the one or more pins of cable 66 (which in turn are in electrical communication with the pins of outlet 64). If patient support apparatus 20 is coupled to outlet 64 wirelessly by way of an adjacent locator unit 60, controller 140 sends a message to locator unit 60 (via Bluetooth transceiver 128 and/or one or more UWB transceivers 132) instructing controller 112 to control headwall interface 118 such that the electrical state of one or more pins of outlet 64 is changed. In many conventional outlets 64, nurse call signals are communicated by changing the electrical state of pin 25 (nurse call +) relative to a common pin, or pin 26 (Nurse Call Normally Open/Normally Close). Of course, patient support apparatus 20 and headwall interface 118 may be configured to change the electrical state of one or more other pins in response to a nurse call signal (from control 50*g* or nurse call device 150), depending upon the particular communication outlet 64 that is installed within a particular healthcare facility.

Regardless of which pin or pins have its/their electrical state(s) changed, conventional nurse call systems 70 are configured to detect these changes in electrical state and to provide a signal at one or more nurses' stations 78 indicating that a patient in a particular room is requesting to speak with a nurse. The nurse call system 70 allows the nurse to answer this call, such as by picking up a telephone handset, or in other manners. Once the nurse answers this call, audio communication between the nurse and the patient can be carried out over conductors 68. That is, electrical signals corresponding to the nurse's voice are sent over conductors 68 to communication outlet 64 on specific pins (typically pins 8 and 9, although other pins may be used), and these are then forwarded to patient support apparatus 20, either through a cable 66 that is coupled to patient support apparatus 20 and outlet 64, or through locator unit 60 (if cable 66 is coupled between locator unit 60 and outlet 64). When locator unit 60 is plugged into outlet 64 by way of cable 66, controller 112 transmits the audio signals corresponding to the nurse's voice to patient support apparatus 20 by Bluetooth transceiver 106. Controller 140 of patient support apparatus 20 then either sends these audio signals to an onboard speaker (not shown) or transmits them to nurse call device 150. Controller 150 makes this routing decision based on whether the nurse call signal was caused by the activation of an onboard control 50*g*, or by the receipt of a nurse call signal from nurse call device 150. That is, if the nurse call signal originated from nurse call device 150, controller 140 sends the audio signals to nurse call device 150 via Bluetooth transceiver 128, and nurse call device 150 then sends these audio signals to speaker 162, which converts these audio signals to sound waves that the patient can hear. If the nurse call signal originated from the patient activating an onboard nurse call control 50*g*, controller 140 sends the audio signals to an onboard speaker, which also converts the audio signals to sound waves that the patient can hear.

In addition to forwarding the audio signals from the remote nurse to a speaker onboard patient support apparatus 20 or nurse call device 150, controller 140 is configured to send patient voice signals to the nurse call system. These patient voice signals may be detected by microphone 142 onboard patient support apparatus 20 (when the patient is positioned onboard patient support apparatus 20), or by microphone 162 when the patient is positioned near nurse call device 150. However detected, controller 140 forwards them to appropriate pins of outlet 64, either through nurse call cable 66 or through locator unit 60. Bidirectional communication between the patient and the nurse can therefore be established when the patient is positioned on the bed, as well as when the patient is positioned adjacent to nurse call device 150.

Nurse call device 150 is designed to be a portable device that may be applied to structures that otherwise don't have the functionality built into them to allow a patient to use them to summon a nurse. As will be discussed, in some embodiments, nurse call device 150 may include an adhesive material, or other fastening structure, that allows it to be coupled to such a structure. In still other embodiments, nurse call device 150 may be coupled to a structure that is carried by the patient, such as by attaching it to a necklace, a wristband, an item of clothing, or to some other structure that is carried by, worn, or otherwise moved with the patient. Still further, nurse call device 150 may be a complete standalone device that is positioned at a location that is spaced from patient support apparatus 20 and that is in an area where a patient may tend to be located.

In a given healthcare facility, there may be multiple nurse call devices 150 positioned therein. Additionally, at any given time, there may be multiple nurse call devices 150 that are positioned within communication range of a particular patient support apparatus 20. Patient support apparatus 20 is configured to only forward nurse call signals to nurse call system 70 that it receives from an associated nurse call device 150. Indeed, patient support apparatus 20 may be configured to ignore communications from all nurse call devices 150 that are disassociated from that patient support apparatus 20. Patient support apparatus 20 is also configured to communicate audio signals of the patient's voice from, and/or the nurse's voice to, the nurse call device 150 that it is currently associated with. Patient support apparatus 20 does not communicate audio signals, either to or from, nurse call devices 150 that it is currently disassociated with.

The manner in which controller 140 associates and disassociates a nurse call device 150 with and from patient support apparatus 20 will now be described. The association process is carried out by a user physically bringing the nurse call device 150 within a near field range 168 (FIG. 5) of patient support apparatus 20. Near field range 168 may be on the order of several inches and will be depend upon the design and construction of near field transceivers 144 and 158, which may be conventional near field transceivers. When near field transceiver 158 of nurse call device 150 is brought within range 168 of near field transceiver 144 onboard patient support apparatus 20, the two transceivers 144 and 158 automatically communicate with each other using near field communication. During such communication, near field transceiver 158 of nurse call device 150 transmits its unique identifier 166 to patient support apparatus 20, and controller 140 of patient support apparatus 20 retains this identifier 166 in memory 134. In some embodiments, near field transceiver 144 of patient support apparatus 20 may forward its unique patient support apparatus identifier 130 to near field transceiver 158 of nurse call device 150, and controller 156 of nurse call device 150 may place the identifier 130 in a memory (not shown). In some embodiments, near field transceiver 144 may be integrated into one or more of, or multiple near field transceivers 144 may be integrated into one or more of, siderails 36, headboard 32, footboard 34, and/or other locations on patient support apparatus 20.

Figure 10:
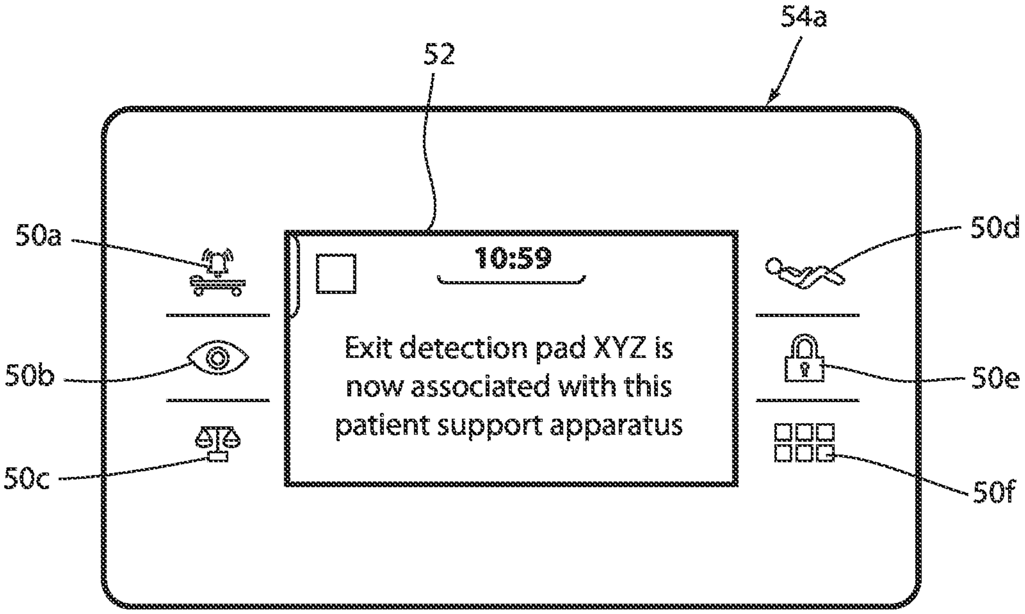
FIG. 10 is a plan view of the caregiver control panel of the patient support apparatus showing a first illustrative message when a device is automatically associated with the patient support apparatus.
Figure 11:
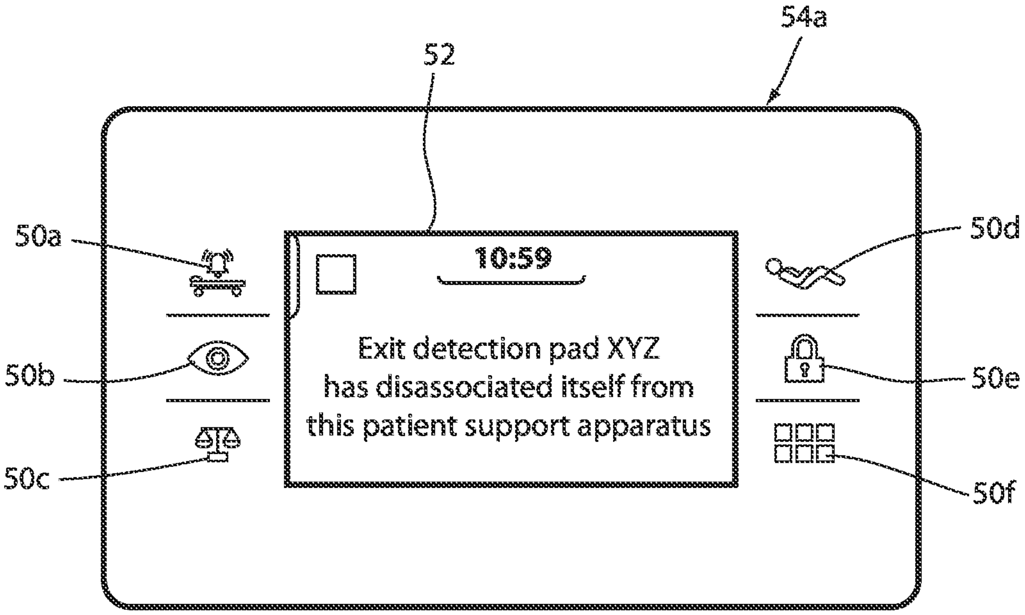
FIG. 11 is a plan view of the caregiver control panel of the patient support apparatus showing a second illustrative message when a device is automatically disassociated from the patient support apparatus.

In some embodiments, after patient support apparatus 20 receives the identifier 166 of nurse call device 150 via near field transceiver 144, controller 140 automatically associates that nurse call device 150 with patient support apparatus 20. Still further, controller 140 may display a message on display 52 (and/or display device 56) indicating that the nurse call device 150 has now been successfully associated with patient support apparatus 20. FIG. 10 illustrates an example of such a message for the successful association of an exit detection sensor 100 with patient support apparatus 20. A similar message may be displayed on display 52 in response to the successful association of a nurse call device with patient support apparatus 20. A message similar to what is shown in FIG. 11 may also be displayed on display 52 (and/or display device 56) when controller 140 disassociates a nurse call device 150 from patient support apparatus 20.

Once nurse call device 150 is associated with patient support apparatus 20, it thereafter remains associated with patient support apparatus 20 until it moves outside of a volume of space 152*b* (FIGS. 4 & 6). Once nurse call device 150 moves outside of volume of space 152*b*, controller 140 is configured to automatically disassociate the nurse call device 150 from patient support apparatus 20. Controller 140 repetitively determines and monitors the position of nurse call device 150 after it has associated the nurse call device 150 with patient support apparatus 20. Controller 140 uses UWB transceivers 132, which communicate with UWB transceiver 154 onboard nurse call device 150, to repetitively determine the relative position of nurse call device 150 with respect to patient support apparatus 20. Controller 140 compares this relative position to space volume 152*b* and, if it is outside of space volume 152*b*, it automatically disassociates nurse call device 150 from patient support apparatus 20. On the other hand, as long as the position of nurse call device 150 remains inside of space volume 152*b*, controller 140 maintains the association of nurse call device 150 with patient support apparatus 20.

If a patient presses nurse call button 160 on nurse call device 150, nurse call device 150 forwards a nurse call signal to patient support apparatus 20. This nurse call signal may be specifically addressed to the specific patient support apparatus 20 with which nurse call device 150 is associated with (using, for example, patient support apparatus ID 130 that it may have received during the near field association process), or it may be broadcast without any specific address. In either case, the nurse call signal includes the identifier 166 of nurse call device 150. When patient support apparatus 20 receives this nurse call signal, it checks the identifier 166 contained within the nurse call signal to see if it matches the identifier 166 of an associated nurse call device 150. If it matches, controller 140 forwards the nurse call signal to outlet 64 in one of the manners previously described. If the identifier 166 does not correspond to a currently associated nurse call device 150, controller 140 does not forward the nurse call signal to outlet 64.

Space volume 152*b* (FIGS. 4 & 6) is defined with respect to patient support apparatus 20 and therefore moves as patient support apparatus 20 moves. Space volume 152*b* is generally sized such that it encompasses substantially all of the room 58 in which patient support apparatus 20 is positioned, or at least that portion of the room in which nurse call device 150 is expected to be located. When nurse call device 150 is intended to be coupled to a secondary patient support apparatus 20*a*, such as a chair or recliner, space volume 152*b* is selected to have a size that encompasses those areas of room 58 in which a chair or recliner is positioned, or likely to be positioned. In some situations, space volume 152*b* may be large enough to extend into adjacent rooms 58, and this will not affect the proper performance of nurse call device 150 so long as access to those rooms cannot be obtained without moving nurse call device 150 outside of space volume 152*b*. In other words, space volume 152*b* may be advantageously defined such that, when nurse call device 150 is moved out of room 58 through a doorway, the nurse call device 150 will necessarily move outside of space volume 152*b*, thereby causing it to become disassociated from the patient support apparatus 20.

In some embodiments, space volume 152*b* may be defined with one or more static dimensions. In other embodiments, patient support apparatus 20 and/or patient support apparatus server 84 may be configured to allow authorized individuals to change one or more dimensions of space volume 152*b*. Still further, in some embodiments, space volume 152*b* may have variable dimensions based upon the specific room, bay, or other location, that it is currently positioned at. In these embodiments, controller 140 may utilize a table stored in memory 134 that defines the dimensions of space volume 152*b* based on the current location of patient support apparatus 20. The location of patient support apparatus 20 may be determined by controller 140 from the locator unit ID 122 that it receives from an associated locator unit 60, and/or it may be derived from information received from patient support apparatus server 84.

Volume of space 152*b* may different from volume of space 152*a* (and, as will be discussed in greater detail below, volume of space 152*c*). FIG. 6 illustrates an example of an arbitrary healthcare facility room 58 in which is positioned a patient support apparatus 20, a secondary patient support apparatus 20*a*, an exit detection sensor 100, and a nurse call device 150. FIG. 6 also illustrates a first volume of space 152*a*, a second volume of space 152*b*, and a third volume of space 152*c*. First volume of space 152*a*, as has been discussed, is used to determine whether patient support apparatus 20 should associate or disassociate itself from the locator unit 60 that is positioned adjacent to, or inside of, first volume of space 152*a*. Second volume of space 152*b* is used by controller 140, as has been noted, to determine whether to associate or disassociate nurse call device 150 with patient support apparatus 20. Third volume of space 152*c* may be used by controller 140, as will be described in greater detail below, to determine whether to associate or disassociate one or more medical devices with patient support apparatus 20 that are typically placed in close proximity to the patient when used in the care of the patient (as opposed to exit detection sensor 100 and/or nurse call device 150, which may be positioned further away from patient support apparatus 20, such as on a separate patient support apparatus 20*a*). It can therefore be seen that controller 140 of patient support apparatus 20 may be configured to use multiple different criteria for determining whether to associate a device with patient support apparatus 20—one for locator units 60, another for exit detection sensors 100 (and/or nurse call devices 150), another for devices physically supported by, or coupled to, patient support apparatus 20, and/or still other for other types of devices.

As shown in FIG. 6, first volume of space 152*a* is a relatively small volume of space that is either positioned close to, or encompasses, fixed locator 60. Second volume of space 152*b* encompasses a substantial portion of room 58, and third volume of space 152*c* encompasses patient support apparatus 20 and a relatively small amount of space surrounding patient support apparatus 20. This small amount of space around the perimeter of third volume of space 152*c* may be defined with the goal of encompassing IV poles, infusion pumps, or other medical devices that may be used in the care of the patient, but that are not directly supported on patient support apparatus 20.

Returning to FIG. 5, controller 156 of nurse call device 150 may comprise a microcontroller and/or any of the other structures that were mentioned above that comprise controller 140 and/or controller 112. Controller 156 is adapted to send a signal to an associated patient support apparatus 20 in response to the activation of nurse call button 160, as well as to process any voice communications between nurse call device 150 and a remotely positioned nurse. Controller 156 may also, or alternatively, be configured to oversee the operation of UWB transceiver 154, near field transceiver 158, and Bluetooth transceiver 164. In some embodiments, controller 156 uses Bluetooth transceiver 164 to communicate the audio signals of the patient to patient support apparatus 20, as well as to receive the audio signals of the nurse from patient support apparatus 20. The audio signals of the patient are generated by microphone 162 and transmitted to transceiver 128 of patient support apparatus 20, while the audio signals of the nurse are received by Bluetooth transceiver 164 and forwarded to speaker 162 for conversion to sound waves. As shown in FIG. 5, nurse call device 150 includes a microphone and speaker 162 that are combined. In other embodiments, nurse call device 150 may include a separate microphone and a separate speaker.

Patient support apparatus 20 may also, or alternatively, be configured to use UWB transceivers 132 to determine the relative position of one or more external exit detection sensors 100 (FIGS. 5 & 6). External exit detection sensors 100 refer to exit detection sensors that are external to, and separate from, the sensors that are built into exit detection system 136 of patient support apparatus 20. Such external exit detection sensors 100 may include a UWB transceiver 170, a controller 172, a near field transceiver 174, one or more sensors 176, and a unique ID 178 that uniquely identifies each exit detection sensor 100. UWB transceiver 170 is adapted to communicate with the UWB transceivers 132 positioned onboard patient support apparatus 20 so that the position of exit detection sensor 100 relative to patient support apparatus 20 can be repetitively determined. UWB transceiver 170 may be the same as all of the other UWB transceivers discussed herein (e.g. UWB transceivers 132, 104, 154, etc.). UWB transceiver 170 is further adapted to transmit the unique ID 178 to patient support apparatus 20 so that patient support apparatus 20 knows which specific exit detection sensor 100 it is communicating with. Controller 140 may use this ID 178 to keep track of which, if any, exit detection sensors 100 it is currently associated with.

Controller 172 of exit detection sensor 100 is adapted to oversee the operation of exit detection sensor 100, to process the output(s) of sensor(s) 176, and to control the communication carried out by UWB transceiver 170 and near field transceiver 174. Sensor(s) 176 may include one or more sensors of different type that are adapted to detect the presence or absence of a patient from a patient support apparatus, such as secondary patient support apparatus 20*a*. In some situations, sensors 176 may include one or more force sensors that are adapted to detect the weight of a patient when the patient is supported on top of exit detection sensor 100. Alternatively, sensor(s) 176 may comprise one or more infrared sensors, one or more cameras, and/or other types of sensors that are adapted to detect the presence and absence of a patient when the patient is positioned on secondary patient support apparatus 20*a*.

Figure 7:
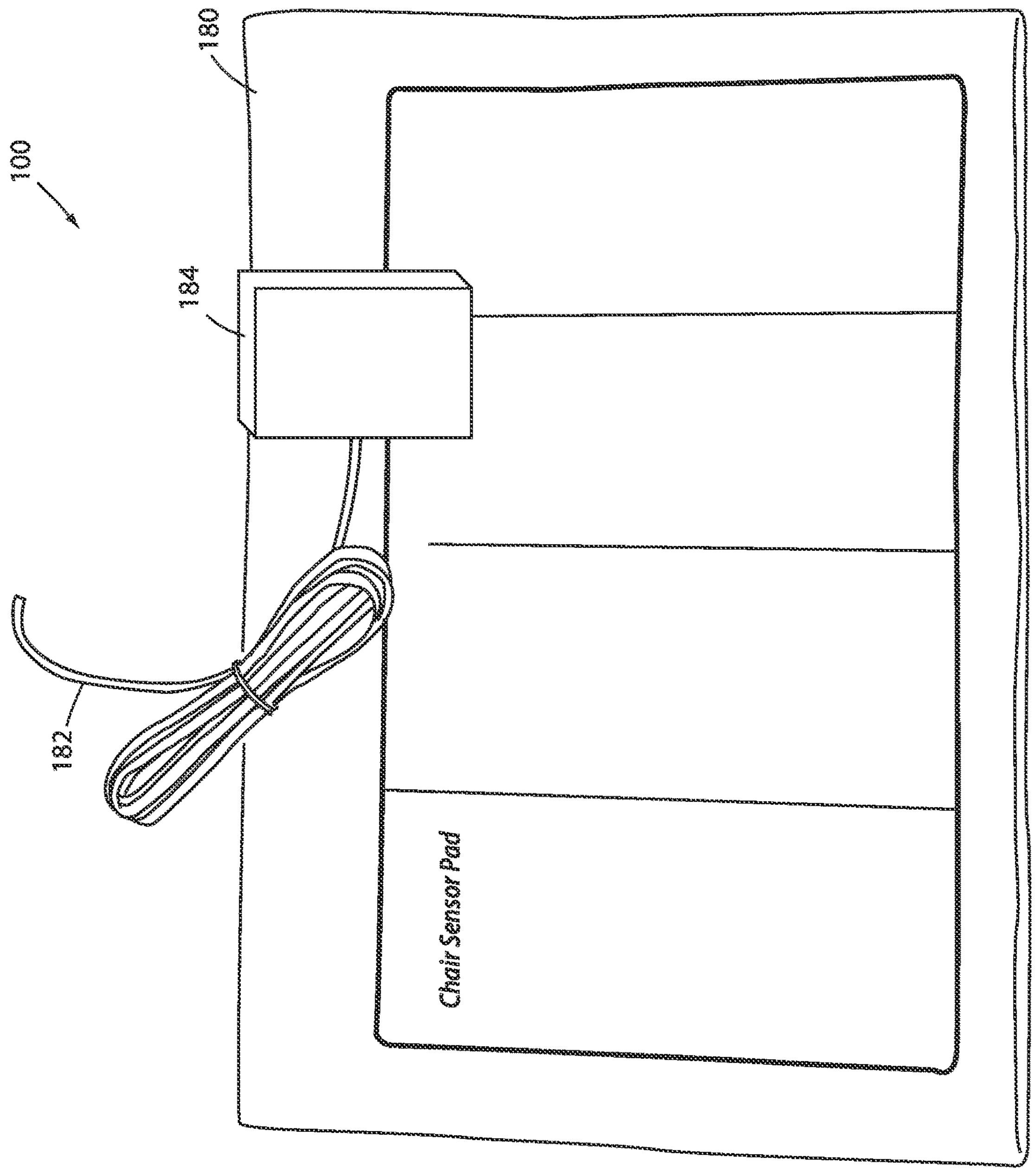
FIG. 7 illustrates an example of a portable exit detection sensor.

In some embodiments, exit detection sensor 100 includes an exit detection pad 180, one example of which is shown in FIG. 7. As shown therein, exit detection sensor 100 includes a pad 180, a cable 182, and a control unit 184. Control unit 184 houses UWB transceiver 170, controller 172, identifier 179 and, in some embodiments, near field transceiver 174. The pad 180 itself houses sensors 176. Pad 180 is adapted to be placed on top of, or underneath, a cushion that the patient sits on when seated in a patient support apparatus (whether a primary patient support apparatus 20 or a secondary patient support apparatus 20*a*). In such embodiments, sensors 176 detect the weight of the patient when he or she is sitting or lying down on the cushion. The cushion may be a mattress, a chair cushion, or any other type of soft support that is adapted to provide support to the patient in a comfortable manner. When the patient exits the patient support apparatus on which pad 180 is positioned, sensors 176 detect the reduced (or completely absent) patient weight, and controller 172 is adapted to issue an exit alert.

Controller 172 is configured to issue the exit alert by sending an exit detection message (using UWB transceiver 170) to patient support apparatus 20 that informs patient support apparatus 20 of the exit alert (and that includes ID 178). Controller 140 of patient support apparatus 20 responds to the exit detection message in the same manner that it responds to an exit detection alert made by onboard exit detection system 136. That is controller 140 is configured to issue a local alert (such as by issuing one or more sounds, flashing one or more lights, displaying one or more messages on display 52, and/or taking other actions), as well as to transmit a remote alert to nurse call system 70. Controller 140 transmits the remote alert to nurse call system 70 by changing the electrical state of one or more pins of communication outlet 64. If patient support apparatus 20 is connected to outlet 64 by way of cable 66, controller 140 may change the state of one or more relays onboard patient support apparatus 20 that are in electrical communication with one or more pins of cable 66. If patient support apparatus 20 is connected to outlet 64 by way of a wireless connection to a locator unit 60, controller 140 sends an exit detection message to locator unit 60 (using Bluetooth transceiver 128 and/or one or more UWB transceivers 132), which responds by instructing headwall interface 118 to change the electrical state of one or more of the pins of communication outlet 64.

It can be seen from the foregoing description that, by adding exit detection sensor 100 to a secondary patient support apparatus 20*a*, the secondary patient support apparatus 20*a* not only gains the ability to detect a patient's exit therefrom, but the exit detection sensor 100 also piggybacks off the primary patient support apparatus 20 for communicating the exit detection alert to nurse call system 70. That is, even though the secondary patient support apparatus 20*a* does not include any cable 66 or ability to communicate directly with a locator unit 60 (or communication outlet 64), the exit detection sensor 100 is able to utilize the communication channel of primary patient support apparatus 20 with nurse call system 70 to forward the exit detection alert to nurse call system 70. In this manner, remotely positioned nurses are still able to be informed of patient exits from secondary patient support apparatus 20*a*, even in situations where the healthcare facility room 58 has only a single communication outlet 64 (that may be used by primary patient support apparatus 20), and even in situations where secondary patient support apparatus 20*a* has no built-in abilities to communicate with other structures in the room, such as outlet 64 and/or locator unit 60. A healthcare employee merely has to attach exit detection sensor 100 to the secondary patient support apparatus 20*a* and ensure that it has a supply of electrical power (which may include a battery inside of control unit 184 (FIG. 7), or which may include an AC cable to be plugged into an AC wall outlet).

After the healthcare employee attaches exit detection sensor 100 to a patient support, such as a secondary patient support apparatus 20*a*, the exit detection sensor 100 is adapted to automatically forward its exit detection alerts to an associated patient support apparatus 20. The manner in which exit detection sensor 100 is associated with, and disassociated from, a particular patient support apparatus 20 may be the same as the association and disassociation processed described above with respect to nurse call device 150. That is, the association process is carried out by a user physically bringing the exit detection sensor 100 within a near field range 168 (FIG. 5) of patient support apparatus 20. When near field transceiver 174 of exit detection sensor 100 is brought within range 168 of near field transceiver 144 onboard patient support apparatus 20, the two transceivers 144 and 174 automatically communicate with each other using near field communication. During such communication, near field transceiver 174 of exit detection sensor 100 transmits its unique identifier 178 to patient support apparatus 20, and controller 140 of patient support apparatus 20 retains this identifier 178 in memory 134. In some embodiments, near field transceiver 144 of patient support apparatus 20 may forward its unique patient support apparatus identifier 130 to near field transceiver 174 of exit detection sensor 100, and controller 172 of exit detection sensor 100 may place the identifier 130 in a memory (not shown).

In some embodiments, after patient support apparatus 20 receives the identifier 178 of exit detection sensor 100 via near field transceiver 144, controller 140 automatically associates that exit detection sensor 100 with patient support apparatus 20. Still further, and as will be discussed in more detail below, controller 140 may display a message on display 52 (and/or display device 56) indicating that the exit detection sensor 100 has now been successfully associated with patient support apparatus 20. FIG. 10 illustrates an example of such a message for the successful association of an exit detection sensor 100 with patient support apparatus 20. Controller 140 may also display a message, one example of which is shown in FIG. 11, when a nurse call device 150 is automatically disassociated with patient support apparatus 20.

Once exit detection sensor 100 is associated with patient support apparatus 20, it thereafter remains associated with patient support apparatus 20 until it moves outside of a volume of space 152*b* (FIGS. 4 & 6). Once exit detection sensor 100 moves outside of volume of space 152*b*, controller 140 is configured to automatically disassociate the exit detection sensor 100 from patient support apparatus 20. Controller 140 repetitively determines and monitors the position of exit detection sensor 100 after it has associated the exit detection sensor 100 with patient support apparatus 20. Controller 140 uses UWB transceivers 132, which communicate with UWB transceiver 170 onboard exit detection sensor 100, to repetitively determine the relative position of exit detection sensor 100 with respect to patient support apparatus 20. Controller 140 compares this relative position to space volume 152*b* and, if it is outside of space volume 152*b*, it automatically disassociates exit detection sensor 100 from patient support apparatus 20. On the other hand, as long as the position of exit detection sensor 100 remains inside of space volume 152*b*, controller 140 maintains the association of exit detection sensor 100 with patient support apparatus 20. As noted previously, the dimensions of the space volume 152*b* that are used for the association/dissociation process of exit detection sensor 100 may be the same as, or different from, the dimensions of space volume 152*b* that are used for the association/dissociation process of nurse call device 150 and/or other devices that are automatically associated with, and/or disassociated from, patient support apparatus 20.

Returning to FIG. 7, cable 182 couples pad 180 to control unit 184. As was noted, control unit 184 may house UWB transceiver 170, controller 172, identifier 179 and, in some embodiments, near field transceiver 174, and pad 180 (which may contain sensor(s) 176). Control unit 184 may also house one or more batteries (not shown) for providing power to exit detection sensor 100, and/or a power cable may be coupled to control unit 184 to allow it to receive electrical power from a conventional AC outlet. In the embodiment shown in FIG. 7, exit detection sensor 100 does not need to communicate with any electronic system that may be built into secondary patient support apparatus 20*a*, and therefore does not include any connections for, or other means of communicating with, a secondary patient support apparatus 20*a*. Instead, exit detection sensor 100 is adapted to communicate directly with patient support apparatus 20 and notify patient support apparatus 20 when a patient exit is detected by it.

Secondary patient support apparatus 20*a* (FIGS. 4 & 5), in some embodiments, is a recliner, or other chair, that is customarily positioned with the patient's room 58. Secondary patient support apparatus 20*a* differs from primary patient support apparatus 20 in that it typically doesn't include as much functionality, it typically doesn't include any exit detection functionality or nurse call functionality (unless an exit detection sensor 100 or nurse call device 150 are added to it), it typically is not intended for the patient to sleep in, and it typically does not include circuitry for communicating with communications outlet 64 (other than if exit detection sensor 100 or nurse call device 150 are added to it). Secondary patient support apparatus 20*a* may be intended to provide an alternative resting spot for a patient while he or she is in a healthcare facility, thereby helping to promote movement of the patient. Secondary patient support apparatus 20*a* may take on other forms besides a chair or recliner.

As shown in FIG. 5, secondary patient support apparatus 20*a* may include a controller 186, a UWB transceiver 188, and an identifier 190. Secondary patient support apparatus 20*a* may also include additional components, such as, but not limited to, any of the components of primary patient support apparatus 20. In some embodiments, secondary patient support apparatus 20*a* may include any or all of the components of the recliners disclosed in any of the following commonly-assigned U.S. patents: U.S. Pat. No. 9,713,559 issued July 25 to Christopher Hough et al. and entitled MEDICAL SUPPORT APPARATUS; U.S. Pat. No. 9,782,005 issued Oct. 10, 2017, to inventors Anish Paul et al. and entitled MEDICAL SUPPORT APPARATUS; and U.S. Pat. No. 10,330,522 issued Jun. 25, 2019, to inventors Anish Paul et al. and entitled PERSON SUPPORT APPARATUS WITH EXIT DETECTION SYSTEM AND/OR SCALE SYSTEM, the complete disclosures of all of which are incorporated herein by reference. Secondary patient support apparatus 20*a* may take on still other forms.

In some embodiments, secondary patient support apparatus 20*a* omits identifier 190 and UWB transceiver 188, as indicated by the dashed lines in FIG. 5. In such embodiments, controller 186 is not able to communicate with UWB transceivers 132 positioned onboard primary patient support apparatus 20. However, if a nurse call device 150, an exit detection sensor 100, and/or a UWB tag is added to secondary patient support apparatus 20*a*, then the device 150, sensor 100, and/or tag will be able to communicate with UWB transceivers 132 and controller 140 of primary patient support apparatus 20, and controller 140 will be able to determine the location of not only device 150, sensor 100, and/or the tag, but also, by proxy, the position of the secondary patient support apparatus 20*a* to which the device 150, sensor 100, and/or tag is attached.

Controller 186 (FIG. 5), which may include one or more microcontrollers and/or which may take on any of the above-described forms of controllers 112, 140, 156, and/or 172, is adapted to oversee the operation of secondary patient support apparatus 20*a*. In some embodiments, secondary patient support apparatus 20*a* includes one or sensors and controller 186 is adapted to forward data from one or more of those sensors to primary patient support apparatus 20. Primary patient support apparatus 20 may forward some or all of this data to patient support apparatus server 84, may display some or all of this data on its display 52, may forward some or all of this data to display device 56 (via an associated locator unit 60), and/or it may forward some or all of this data to EMR server 92. When secondary patient support apparatus 20*a* includes a brake, an electrical cable, an exit detection system, a patient presence detector, a timer, and/or one or more actuators for moving a seat, backrest, and/or leg rest, controller 186 may be adapted to forward data regarding the brake (on or off), the electrical cable (plugged in or unplugged), the exit detection system (armed or disarmed; alarming or not alarming), the current presence or absence of the patient on secondary patient support apparatus 20*a*, the amount of time the patient has been present in, or absent from, secondary patient support apparatus 20*a*, and/or the position and/or orientation of the actuators and/or the position and/or orientation of one or more components of secondary patient support apparatus 20*a* (e.g. the seat, backrest, and/or leg rest). Still other data may be forwarded by controller 186 to primary patient support apparatus 20 using UWB transceivers 188 or, in some embodiments, one or more other transceivers that may be incorporated into secondary patient support apparatus 20*a*, such as, but not limited to, a Bluetooth transceiver.

As was noted, the particular embodiment of secondary patient support apparatus 20*a* shown in FIG. 5 does not include an exit detection sensor or a nurse call device. However, if a caregiver wishes to modify secondary patient support apparatus 20*a* to include an exit detection functionality and/or a nurse call functionality, he or she can add exit detection sensor 100 and/or nurse call device 150 to secondary patient support apparatus 20*a*. Exit detection sensor 100 can be added by first associating it with primary patient support apparatus 20 using near field transceivers 174 and 144 (described above) and then placing it under, or on top of, the seat area of secondary patient support apparatus 20*a*. Nurse call device 150 can be added to secondary patient support apparatus 20*a* by first associating it with primary patient support apparatus 20 using near field transceiver 158 and 144 (described above), and then attaching it to any convenient location of secondary patient support apparatus 20*a*. Once either of these devices are attached and associated, they provide secondary patient support apparatus 20*a* with the ability to detect patient exits and/or the ability for a patient to summon (and in some embodiments, talk to) a remote nurse. It will be understood that the addition of exit detection sensor 100 and/or nurse call device 150 to secondary patient support apparatus 20*a* does not require any cable connections between these devices and secondary patient support apparatus 20*a*, nor does it require any electronic pairing, or other configuration steps, between these devices and secondary patient support apparatus 20*a*. Indeed, neither exit detection sensor 100 nor nurse call device 150 need to be able to communicate with controller 186 for them to provide their respective exit detection and nurse call functions. This is because, as noted above, exit detection sensor 100 and nurse call device 150 are stand-alone devices that are capable of operating independently of whatever structure (e.g. secondary patient support apparatus 20*a*) that they are attached to.

In those embodiments of secondary patient support apparatus 20*a* that include controller 186 and UWB transceiver 188, it is possible that primary patient support apparatus 20 may receive three separate streams of data from secondary patient support apparatus 20*a*. The first stream may come from UWB transceiver 188, and this stream may include data regarding the various components of secondary patient support apparatus 20*a*, as discussed above. The second stream may come from a UWB transceiver 170, if an exit detection sensor 100 is coupled to secondary patient support apparatus 20*a*. And the third stream may come from a UWB transceiver 154 if a nurse call device 150 is coupled to secondary patient support apparatus 20*a*. Of course, primary patient support apparatus 20 may receive fewer streams of data if exit detection sensor 100 and/or nurse call device 150 are not coupled to secondary patient support apparats 20*a*, and/or if secondary patient support apparatus 20*a* does not include UWB transceiver 188.

Controller 140 of patient support apparatus 20 (FIG. 5), in addition to determining the relative location of UWB transceivers 154, 170, 188, and/or 104, may also be configured to determine the location of UWB transceivers that are attached to other devices and/or that are incorporated into UWB tags that are attached to other devices. Such UWB tags may take on any of the forms of the tags described in commonly assigned U.S. patent application Ser. No. 63/193,777 filed May 27, 2021, by inventors Thomas Deeds et al. and entitled SYSTEM FOR ASSOCIATING MEDICAL DEVICE DATA, the complete disclosure of which is incorporated herein by reference. The devices to which such tags may be attached, or into which a UWB transceiver may be built, include, but are not limited to, any one or more of the following: a secondary patient support apparatus 20*a*, an infusion pump, a vital sign sensor, an exercise device, a heel care boot, an IV stand and/or pole, a ventilator, a DVT pumps, a patient monitor (e.g. a saturated oxygen ($SpO_2$) monitor, an EKG monitor, a vital sign monitor, etc.), a patient positioning devices (e.g. a wedge, turning device, pump), an ambient sensor (e.g. air temperature, air flow, light, humidity, pressure, altitude, sound/noise), a mattress 42, an incontinence pad or one or more sensors adapted to detect patient incontinence, a Holter device adapted to monitor and record a patient's heart signals, a patient ID tag or bracelet worn by the patient that identifies the patient, a caregiver tag or ID bracelet worn by a caregiver that identifies the caregiver, a patient temperature management device (or associated device, such as a one or more hoses, thermal wraps, etc.), one or more mobility assistance devices that a patient may be expected to use, and/or other types of devices. Alternatively, or additionally, any of these devices may be constructed to include one or more built-in UWB transceivers that are adapted to communicate with UWB transceivers 132 positioned on board patient support apparatus 20.

In some embodiments, after determining that the relative location of one or more of these devices is within a corresponding space volume 152, controller 140 forwards a message to patient support apparatus server 84 indicating that these devices (whose IDs are included in the message) are currently located in the same room as patient support apparatus 20. Patient support apparatus server 84 may forward this information to one or more of electronic devices 98, thereby enabling authorized individuals to track the location of pieces of equipment within the healthcare facility. Controller 140 may therefore, in addition to determining the location of UWB-enabled devices for purposes of communicating data to/from those devices, also determine the location of those devices for tracking purposes. Patient support apparatus 20 therefore can facilitate the tracking of a variety of equipment used within the healthcare facility.

By including a tag on such devices and/or a built-in UWB transceiver, controller 140 is able to automatically associate and disassociate patient support apparatus 20 with any of these devices. The automatic association may be accomplished by the device or tag moving inside of a predetermined volume of space defined with respect to patient support apparatus 20 (e.g. one of space volumes 152*b*, 152*c*, or another space volume), or within a predetermined volume of space defined with respect to another structure (e.g. locator unit 60 and space volume 152*a*, and/or another space volume). The automatic disassociation may be accomplished by the device or tag moving outside of the same predetermined volume of space. Alternatively, controller 140 may use modified volumes of space-such as, but not limited to, larger space volumes-when automatically determining whether to disassociate one of these devices or tags from patient support apparatus 20. In other words, once a device or tag has been determined to be positioned inside of a particular volume of space, such as space volume 152*b* or 152*c* (and any additional association conditions are met, if there are any), and controller 140 has associated the tag or device with patient support apparatus 20, controller 140 may thereafter increase the size of—and/or otherwise change one or more dimensions of—the volume of space when determining whether to disassociate the device. In this manner, the volumes of space 152 may have a sort of hysteresis aspect wherein a device or tag has to be positioned inside of a smaller space volume in order to be associated with patient support apparatus 20, but thereafter can only be disassociated if it moves outside of a larger sized volume of space. In still other embodiments, the dimensions of one or more of the volumes of space are the same for both association and disassociation purposes.

In general, the tags discussed herein include a UWB transceiver that is able to communicate with each UWB transceiver 132 onboard patient support apparatus 20. This communication enables controller 140 of patient support apparatus 20 to determine the distances between each UWB transceiver 132 and the tag. By knowing these distances, as well as the location of each transceiver 132 on patient support apparatus 20, controller 140 is able to determine the relative position of the tag with respect to patient support apparatus 20, including whether the tag is positioned inside or outside of a particular space volume 152.

In some embodiments, UWB transceivers 104, 132, 154, 170, and 188 (FIG. 5) may operate in the same manner as, and include any of the same functions as, the anchors and pseudo-anchors disclosed in commonly assigned U.S. patent application Ser. No. 63/193,777 filed May 27, 2021, by inventors Thomas Deeds et al. and entitled SYSTEM FOR ASSOCIATING MEDICAL DEVICE DATA, the complete disclosure of which has already been incorporated herein by reference. In some embodiments, locator units 60 may also be configured to determine the location of a device (e.g. exit detection sensor 100, nurse call device 150, etc.) in any of the manners disclosed in commonly assigned U.S. patent application Ser. No. 63/132,514 filed Dec. 31, 2020, by inventors Alexander Bodurka et al. and entitled PATIENT SUPPORT APPARATUS AND MEDICAL DEVICE NETWORKS, and in commonly assigned U.S. patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosures of both of which are incorporated herein by reference.

Display device 56 (FIG. 5) includes a display controller 192 and a display 194. Display device 56 differs from the other devices and/or tags discussed herein in that it does not need to include a UWB transceiver, such as is found in these other devices and/or tags. This is because patient support apparatus 20 is not configured to determine the location of display device 56. Instead, controller 140 of patient support apparatus 20 is configured to use UWB transceivers 132 to determine the location of the locator unit 60 to which the display device 56 is coupled. If the patient support apparatus 20 (or a reference point on it) and locator unit 60 are not both positioned within the space volume 152*a*, the controller 140 will not send data to be displayed to the locator unit 60. If the locator unit 60 and patient support apparatus 20 (or a reference point on it) are both positioned within the space volume 152*a*, controller 140 is configured to be able to send data to be displayed on the coupled display device 56 by forwarding the data to be displayed to the associated locator unit 60, which then forwards it to display device 56 via video port 120 and video cable 110. In some embodiments, controller 140 forwards the data to be displayed on display device 56 to the associated locator unit 60 by using Bluetooth transceiver 128, while in other embodiments it may use a UWB transceiver 132, or another type of transceiver. The forwarding of data to be displayed on display device 56 is a direct forwarding of data from patient support apparatus 20 to locator unit 60, and from there to display device 56, with no other intermediaries, in at least some embodiments.

Because display device 56 need not include a UWB transceiver, display device 56 may be a conventional television, computer monitor, or other conventional device, that is capable of displaying the video signals that are transmitted over video cable 110. In addition, it is not necessary for display device 56 to execute any specialized software app that authenticates communication with the coupled locator unit 60 and/or with patient support apparatus 20. Instead, once controller 140 determines that both patient support apparatus 20 (or a reference point thereon) and locator unit 60 are within space volume 152*a*, controller 140 need not perform any additional security protocols regarding display device 56. Indeed, controller 140 does not need to be able to perform any communications with display device 56 other that forwarding data to be displayed to the associated locator unit 60. In this manner, display device 56 need not know anything about locator unit 60 and/or patient support apparatus 20. It merely displays the video signal coming from video cable 110, and therefore does not need a software app that is specialized to patient support apparatus 20 and/or to locator unit 60 and/or to UWB communications.

It should also be noted that the display of data on display 52 and/or display device 56 from an associated device is carried out by patient support apparatus 20 automatically. That is, for example, when a user has configured patient support apparatus 20 to display data from secondary patient support apparatus 20*a* on a display device 56, it automatically forwards this data to the associated display device 56. Similarly, if a patient with a UWB-tagged heart rate monitor is wheeled into a bay area of a patient room that includes a display device 56 coupled to a locator unit 60, controller 140 is configured to automatically start displaying the patient's heart rate information on that display device 56 as soon as patient support apparatus 20 completes the following two association processes: (1) the association between patient support apparatus 20 and the locator unit 60 to which display device 56 is coupled, and (2) the association between patient support apparatus 20 and the heart rate monitor. In this manner, the caregiver sees the patient's heart rate data displayed on the display device 56 within seconds after moving the patient support apparatus 20 into the bay area, and the caregiver doesn't need to connect any cables, press any buttons, or take any other actions, in order for the heart rate data to be displayed on display device 56. Similarly, when the patient support apparatus 20 moves out of the bay area, the display of the patient's data on the display device 56 automatically terminates. This automatic termination is carried out after patient support apparatus 20 moves outside of the space volume 152*a* associated with the locator unit 60 to which the display device 56 is connected. Once outside of this space volume 152*a*, controller 140 disassociates patient support apparatus 20 from that locator unit 60 and its associated display device 56, and once this disassociation occurs, it stops sending data to be displayed on display device 56.

As another example of the automatic display of device data on a display, if a caregiver approaches a patient support apparatus 20 while carrying a portable electronic device 98—such as a smart phone or tablet computer that includes a display, a UWB transceiver, and the appropriate software app-controller 140 is adapted to automatically start forwarding the data to the portable electronic device 98 for display on its screen. In this manner, a caregiver that brings his or her portable electronic device within space volume 152*b* (or another space volume defined for such devices 98) can have that patient's heart rate data (and/or other data, such as from secondary patient support apparatus 20*a*, exit detection sensor 100, and/or nurse call device 150) automatically displayed on his/her device. When the caregiver moves his or her portable electronic device 98 outside of the space volume 152*b*, the display of that patient's data automatically ceases because controller 140 automatically disassociates patient support apparatus 20 from the portable electronic device 98 and stops sending it data to be displayed. If the caregiver then moves to another patient's patient support apparatus 20 and steps inside the space volume 152*b* of that patient support apparatus, he or she will automatically see the data from the medical devices associated with that patient displayed on his or her portable electronic device 98.

In some embodiments, controller 140 may be configured to display data from a device associated with patient support apparatus 20, and/or process the data from the associated device, in any of the manners disclosed in commonly assigned U.S. patent application Ser. No. 63/306,279 filed Feb. 3, 2022, by inventors Madhu Sandeep Thota et al. and entitled COMMUNICATION SYSTEM FOR PATIENT SUPPORT APPARATUSES, the complete disclosure of which is incorporated herein by reference.

In some embodiments, patient support apparatus 20 is configurable by a user (e.g. via control panel 54*a*) to control what information, if any, patient support apparatus 20 will send to an associated display device 56, to patient support apparatus server 84, and/or to EMR server 92. Thus, a user can instruct patient support apparatus 20, for example, to send blood pressure readings, breathing rate readings, and pulse rate readings from UWB-tagged vital sign sensors (that are associated with patient support apparatus 20) to EMR server 92, but not status data from secondary patient support apparatus 20*a*. As another example, patient support apparatus 20 is configurable by a user such that controller 140 will send secondary patient support apparatus data to display device 56 and patient support apparatus server 84, but not send any data from exit detection sensor 100 to any associated display devices 56.

Locator units 60 are configured to send a message to patient support apparatuses 20 indicating whether or not a display device 56 (FIGS. 4-5) is coupled thereto via video port 120. In such embodiments, when controller 140 of patient support apparatus 20 receives the signal indicating that a display device 56 is coupled to an associated locator unit 60, it is configured to consult the customized user settings to determine what data, if any, to send to that locator unit 60 for forwarding to the display device 56 coupled to video port 120. It bears noting that, when patient support apparatus 20 associates itself with a particular locator unit 60 that has a display device 56 coupled to its video port 120, it is not necessary for the display device 56 to be positioned within space volume 152*a* in order for controller 140 to send data to be displayed on the display device 56. Instead, controller 140 is configured to only check whether the locator unit 60 is associated with patient support apparatus 20 or not. If it is, controller 140 may send (depending upon the user settings) data to the locator unit 60 for forwarding to the display device 56. If locator unit 60 is not associated with patient support apparatus 20, then controller 140 does not send any data to the locator unit 60 for displaying on display device 56.

In addition to allowing a user to customize what data, if any, that is sent to a display device 56, controller 140 is further configured to allow a user to customize what data is sent to different types of display devices 56. Thus, controller 140 may be programmed to allow a user to send a first set of data to a display device 56 that is coupled to an associated locator unit 60 and a second set of data, different from the first set of data, to a different display, such as, for example, display 52 of patient support apparatus 20 and/or another display, such as, but not limited to, ones that are incorporated into conventional smart phones, laptop computers, tablet computers, smart TVs and/or smart monitors that are either in communication with patient support apparatus server 84 and/or that are positioned within space volume 152, as determined by one or more UWB transceivers coupled to them that are adapted to communicate with UWB transceiver 132 of patient support apparatus 20. It will be appreciated, that in such cases, the conventional smart phone, laptop computer, tablet computer, or other type of display device will include a software app that oversees the UWB communications with patient support apparatus 20 and that controls the display of the data on the display (i.e. screen) of the display device. The software app includes one or more security features built into it that only allow authorized users to have this data displayed on the display device, thereby preventing unauthorized users from viewing this data on their own smart phone, laptop computer, tablet computer, etc. In some embodiments, controller 140 is configured to execute a security check protocol with the display device to authenticate the display device prior to sending it any data for displaying thereon.

Patient support apparatus 20 may include one or more screens that are displayable on display 52 that allow a user to customize the data from associated devices that is shown on display 52 and/or display devices 56. In addition, patient support apparatus 20 is configured to allow the user to change the format and/or layout in which the selected data is to be displayed.

Although secondary patient support apparatus 20*a*, exit detection sensor 100, nurse call device 150, and/or other UWB-equipped devices have been described herein as communicating data directly to an associated patient support apparatus 20, it will be understood that any of these devices (secondary patient support apparatus 20*a*, exit detection sensor 100, nurse call device 150, and/or other UWB-equipped devices) may alternatively, or additionally, communicate such data directly to a locator unit 60 that is associated with them (or that is associated with a patient support apparatus 20 with which they are associated). In such embodiments, patient support apparatus 20 need not act as a conduit for communicating information from these devices to communication outlet 64 and/or display device 56.

Although the foregoing description has primarily indicated that controller 140 determines whether to associate or disassociate patient support apparatus 20 with one or more devices, it will be understood that the association and/or disassociation process may alternatively, partially, and/or additionally, be carried out by patient support apparatus server 84. In such embodiments, controller 140 forwards information to patient support apparatus server 84 so that server 84 can determine whether to associate a particular device with a particular patient support apparatus 20. In such embodiments, server 84 sends a message back to patient support apparatus 20 informing it of what devices it should be associated with, and what devices it should not be associated with.

In some embodiments, server 84 is configured to associate or disassociate devices with specific patients. Server 84 may carry out this patient association and/or disassociation determination by storing in its memory data correlating specific device identifiers (e.g. exit detection sensor identifier 178, nurse call device identifier 166, secondary patient support apparatus identifier 190, etc.)—which are transmitted to patient support apparatus 20 by the device, and then forwarded by patient support apparatus 20 to server 84 via network transceiver 96—with specific patient support apparatus identifiers 130. In order to associate specific devices with a specific patient, patient support apparatus server 84 uses the location identifier 122 that it receives from a specific patient support apparatus 20 to determine the room location of the specific patient support apparatus 20. From this room location, server 84 receives data from a conventional Admission, Discharge, Tracking, or other server that is coupled to network 80 that identifies a specific patient for a specific room (or bay within a room). Server 84 is then able to correlate a specific device (associated with the specific patient support apparatus 20 in that room) with a specific patient identifier because it knows the room (or bay) of the patient support apparatus 20, the specific IDs of the devices associated with that particular patient support apparatus 20, and the patient identifier associated with that particular room (or bay). After associating a device with a particular patient, server 84 is able to automatically retrieve data from a specific patient's medical records stored within EMR server 92 and/or to automatically send data from a particular device to the specific patient's medical records stored in EMR server 92.

Although FIG. 5 illustrates a single exit detection sensor 100, a single nurse call device 150, and a single secondary patient support apparatus 20*a*, it will be understood that this is merely for illustration purposes. Multiple exit detection sensors 100, nurse call devices 150, secondary patient support apparatuses 20*a*, and/or multiple other types of devices, and/or any combinations of these devices, may be in use for a particular patient and controller 140 of patient support apparatus 20 is adapted to determine the locations of those devices relative to space volumes 152*b, c*, etc. and, if they are positioned inside of the corresponding space volume 152, to automatically associate them with patient support apparatus 20 and make their data available for display, forward their data to patient support apparatus server 84, and/or take other actions.

In some embodiments, controller 140 is adapted to automatically associate itself with any one or more of the devices disclosed in commonly assigned U.S. patent application 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosure of which is incorporated herein by reference. Patient support apparatus 20 is configurable by a user to also, or alternatively, automatically display any of the data from these other types of devices on any of the displays 52 and/or associated display devices 56 when these devices are associated with patient support apparatus 20.

Figure 8:
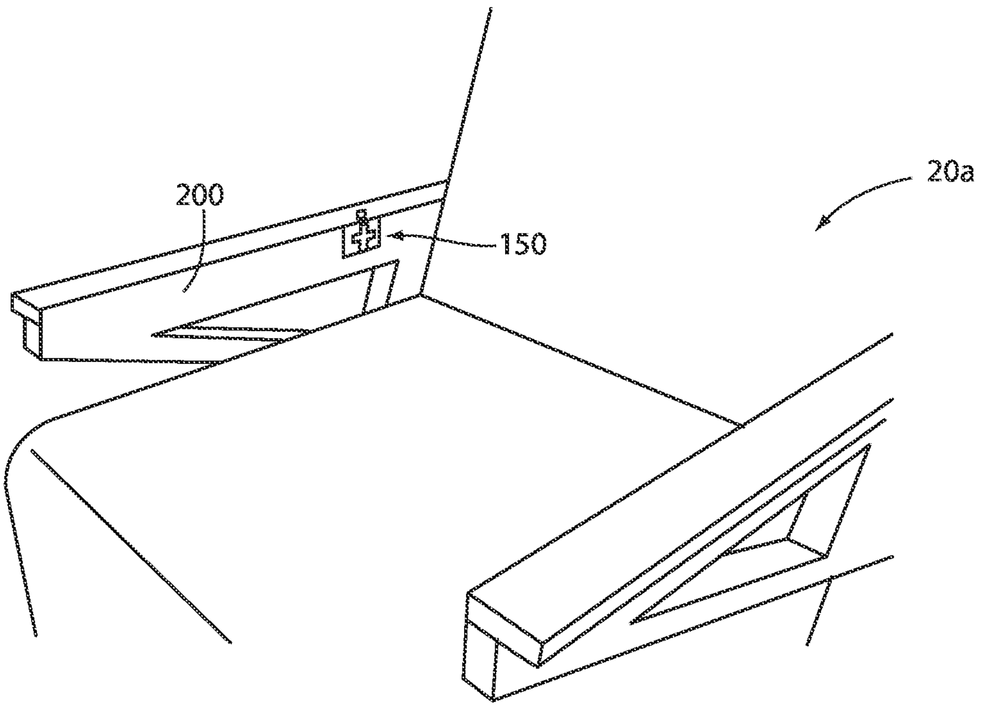
FIG. 8 illustrates an example of a portable nurse call device shown attached to a recliner.
Figure 9:
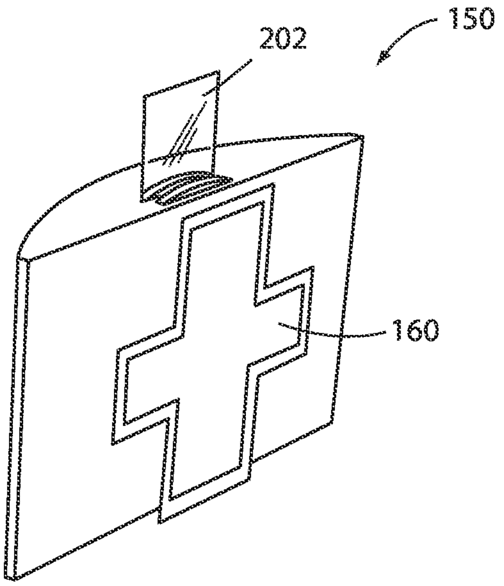
FIG. 9 is a plan view of the portable nurse call device of FIG. 8 shown detached from the recliner.

FIGS. 8 and 9 illustrate one example of a nurse call device 150 that may be coupled to a secondary patient support apparatus 20*a*, or to another structure. FIG. 8 illustrates nurse call device 150 coupled to an armrest 200 of secondary patient support apparatus 20*a*. In some embodiments, nurse all device 150 includes an adhesive coupled to one or more of its sides so that it can be adhesively attached to secondary patient support apparatus 20*a* (or another structure). Alternatively, or additionally, nurse call device 150 may include one or more fasteners and/or it may include one or more hooks, couplers, clamps, hook-and-loop mechanisms, or other structures that enable it to be temporarily, or permanently, affixed to a secondary patient support apparatus 20*a* (or other device).

FIG. 9 illustrates one example of nurse call button 160. When pressed, controller 156 is adapted to send a nurse call signal to patient support apparatus 20, which in turn forwards the signal to communication outlet 64 (directly via cable 66 or indirectly through locator unit 60). Nurse call device 150, as shown in FIG. 9, includes a pull tab 202. Pull tab 202, in some embodiments, is designed to be pulled out of nurse call device 150 prior to use. Tab 202 is positioned inside of device 150 in such a manner that one or more batteries stored therein do not make electrical contact with the electrical components of nurse call device 150, and therefore do not begin to drain themselves until pull tab 202 is removed from device 150. Tab 202 therefore helps preserve the life of any internal batteries until device 150 is actually placed in use.

Nurse call device 150 may be a disposable device that is adapted to be used only for as long as its internal batteries last, for as long as a single patient's visit within the healthcare facility, or for as long as some other defined time period. In some embodiments, nurse call device 150 may be attached to, or include, a chain, strap, or other structure that enables it to be coupled to, or incorporated into, a bracelet or necklace worn by the patient. In this manner, nurse call device 150 travels with the patient so that he or she can summon a nurse, regardless of whether he or she is currently supported on patient support apparatus 20 or 20*a*.

When nurse call device 150 is intended to be worn by a patient, controller 140 may utilize a larger volume of space 152 than it does for nurse call devices 150 that are attached to devices (e.g. secondary patient support apparatus 20*a*). The larger volume of space 152 may be used so that disassociation doesn't occur when the patient visits an adjacent restroom, or otherwise travels outside the volume of space 152*b* used with secondary patient support apparatus 20*a*. Indeed, in some embodiments where nurse call device 150 is adapted to be worn by a particular patient, controller 140 may be configured to not use any space volumes 152 for automatically dissociating the device with patient support apparatus 20. Instead, controller 140 may be configured to retain an association (established by near field transceivers 144 and 158) for the life of the nurse call device 150 and/or until the nurse call device 150 is moved within an association field 168 of a different patient support apparatus 20.

It will be understood that, although FIGS. 4 and 5 illustrate a patient support apparatus 20 that is adapted to automatically monitor the location of exit detection sensor 100, nurse call device 150, and secondary patient support apparatus 20*a*, this is merely one example of the devices whose location patient support apparatus 20 may be configured automatically monitor and/or automatically associate and/or disassociate from. For example, in some embodiments, patient support apparatus 20 may be modified to only monitor the location of exit detection sensors 100, but not nurse call devices 150 and/or secondary patient support apparatuses 20*a*. As another example, another embodiment of patient support apparatus 20 may be configured to monitor the location of nurse call device 150, one or more vital sign sensors, locator units 60, but not exit detection sensors 100 and/or secondary patient support apparatuses 20*a*. Patient support apparatus 20 may be modified to monitor the location(s) of still other devices and/or combinations of devices.

It will be understood that the frequency at which controller 140 repetitively determines the relative location of exit detection sensor 100, nurse call device 150, secondary patient support apparatus 20*a*, locator units 60, and/or other devices, may vary in different embodiments. In some embodiments, this occurs multiple times a second. In other embodiments, this occurs less frequently than once a second. In still other embodiments, the frequency at which controller 140 determines the relative position of a device to patient support apparatus 20 may vary according to the device, the current location of patient support apparatus 20, the movement state of patient support apparatus 20 (i.e. whether it is currently moving or stationary), the brake state of patient support apparatus 20 (i.e. whether the brake is on or off), and/or according to one or more other factors.

Controller 140 is configured (FIGS. 5 and 6) to use the association status of a locator unit 60 to patient support apparatus 20 to determine where to send data to for forwarding to the adjacent communication outlet 64, as well as to determine which locator unit 60 it will accept data from that originated from communication outlet 64. The associated locator unit 60 is therefore the locator unit 60 that patient support apparatus 20 will send the patient's voice signals to (and/or exit detection alerts to, whether from exit detection system 136 or exit detection sensor 100) for forwarding to nurse call system 70. It is also the locator unit 60 that controller 140 will send television commands to when a patient onboard patient support apparatus 20 activates one or more of the television controls 50*l*-50*r*. Similarly, it is the locator unit 60 that controller 140 will send light commands to when a patient onboard patient support apparatus 20 activates one or more or the reading or room light controls 50*s* or 50*t*. The locator unit 60 that patient support apparatus 20 associates itself with is also the locator unit 60 that patient support apparatus 20 will receive audio signals from and direct to its onboard speaker(s) (and/or to nurse call device 150). Such audio signals may correspond to voice signals from a remotely positioned nurse that are forwarded to the corresponding communication outlet 64 by way of nurse call system 70, or such audio signals may correspond to television audio signals that are routed from television 72 to communication outlet 64 by way of the one or more conductors 68.

It will be understood that some of the devices that patient support apparatus 20 can be configured to automatically monitor the location of are devices that may be associated and/or disassociated from patient support apparatus 20 in different manners than exit detection sensor 100 and/or nurse call device 150. That is, controller 140 may be configured to automatically associate some devices with patient support apparatus 20 if they move inside of space volume 152*b*, 152*c*, and/or another space volume, rather than associating them via near field transceiver 144. Controller 140 may be configured to automatically disassociate these devices from patient support apparatus 20 when the device moves outside of the space volume 152*b*, 152*c*, and/or another space volume (which may have an enlarged, or hysteresis-type modification). Alternatively, controller 140 may be configured to associate patient support apparatus 20 with some devices in both manners (near field transceiver 144 and via space volume monitoring).

It will also be understood that the manual association of exit detection sensor 100, nurse call device 150, and/or other devices with patient support apparatus 20 may be carried out in other manners besides using a near field transceiver 144. For example, one manner involves incorporating a bar code scanner into patient support apparatus 20 that is adapted to read a bar code coupled to the device. When the bar code is moved within a detection range of the scanner, the scanner automatically reads the bar code and uses identification information encoded therein to associate that device with patient support apparatus 20.

In some embodiments, when patient support apparatus 20 and/or server 84 associate a device with a particular patient support apparatus 20, controller 140 and/or server 84 are configured to inform medical personnel (via electronic devices 98) that the device is associated with a particular patient support apparatus 20 and/or with a particular patient assigned to that patient support apparatus 20. In this manner, data from the device can be correlated with a particular patient, room location, and/or patient support apparatus 20. Patient support apparatus 20 may therefore be configured to automatically forward data from the associated medical devices to server 84 after the devices become associated with patient support apparatus 20. Such data may, in turn, be automatically forwarded by server 84 to EMR server 92 for entry into the corresponding patient's electronic medical record. In this manner, once controller 140 associates a device with the patient support apparatus 20, data from the device can be automatically recorded in that patient's particular electronic medical record without requiring the caregiver to either manually associate the device with the patient and/or with the patient support apparatus 20 assigned to that patient. In other words, because controller 140 automatically determines that the device is positioned within a corresponding space volume 152, it is not necessary for a caregiver to take any manual steps to ensure that data from the device is forwarded to the proper corresponding patient's electronic medical record because patient support apparatus 20, along with server 84, automatically determine the correct patient associated with that medical device.

In any of the embodiments disclosed herein, server 84 may be configured to additionally execute a caregiver assistance software application of the type described in the following commonly assigned patent applications: U.S. patent application Ser. No. 62/826,97, filed Mar. 29, 2019 by inventors Thomas Durlach et al. and entitled PATIENT CARE SYSTEM; U.S. patent application Ser. No. 16/832,760 filed Mar. 27, 2020, by inventors Thomas Durlach et al. and entitled PATIENT CARE SYSTEM; and/or PCT patent application serial number PCT/US2020/039587 filed Jun. 25, 2020, by inventors Thomas Durlach et al. and entitled CAREGIVER ASSISTANCE SYSTEM, the complete disclosures of which are all incorporated herein by reference. That is, server 84 may be configured to share with one or more electronic devices 98 any of the information shared with the electronic devices disclosed in these aforementioned patent applications. Thus, for example, server 84 may be configured to not only share the location of patient support apparatuses 20 (and any devices that may be associated with them) with electronic devices 98, but it may also forward to devices 98 patient vital sign data, infusion pump data, primary and/or secondary patient support apparatus status data (e.g. current siderail position, bed exit status, brake status, motion lockout status, height status, scale data, etc.) exit detection sensor 100 data, nurse call device 150 data, and/or caregiver rounding data (e.g. when the last rounding was performed for a particular patient, when the next rounds are due, etc.).

In some embodiments, locator units 60 may include additional information stored therein that is shared with patient support apparatus 20 when patient support apparatus 20 becomes associated with the locator unit 60. Such additional information may include location information identifying the relative position of the locator unit 60 with respect to one or more other locator units 60 that are positioned nearby. Additionally or alternatively, the locator units 60 may include information regarding the thickness and/or materials of the wall 62 to which it is attached, wherein such information provides an indication to the patient support apparatus 20 of the amount of attenuation that UWB signals will likely experience when traveling through that wall. Additionally or alternatively, the locator units 60 may include information identifying their general location within the healthcare facility (e.g. room 400, bay A of room 302, hallway X, maintenance area Y, radiology department, emergency department, etc.) and/or information identifying a more specific location of the locator units 60 within the healthcare facility (e.g. a set of X,Y,Z coordinates in a frame of reference that includes all, or a portion of, the healthcare facility; a height on the wall 62, a distance from one or more landmarks and/or architectural features within the healthcare facility, and/or other more specific information). In some embodiments, patient support apparatus 20 is adapted to utilize this information to determine its location within the healthcare facility and/or to determine whether it is positioned on the same side of the wall 62 as a particular locator unit 60. In some embodiments, patient support apparatus 20 and/or locator units 60 include any of the same structures, functions, and/or features of any of the patient support apparatuses and/or wall units disclosed in commonly assigned U.S. patent application Ser. No. 63/245,245 filed Sep. 17, 2021, by inventors Kirby Neihouser et al. and entitled SYSTEM FOR LOCATING PATIENT SUPPORT APPARATUSES, the complete disclosure of which has already been incorporated herein by reference.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a support surface adapted to support a patient;

a first transceiver coupled to a first location on the patient support apparatus, the first transceiver adapted to wirelessly communicate with a second wireless transceiver coupled to an exit detection sensor that is portable and separate from the patient support apparatus;

and a controller adapted to use radio frequency (RF) communication between the first transceiver and the second wireless transceiver to determine a distance between the exit detection sensor and the patient support apparatus, the controller further adapted to receive an exit detection alert signal from the exit detection sensor; to use the distance to determine if the exit detection sensor is positioned inside or outside of a volume of space; if the exit detection sensor is positioned inside the volume of space, to transmit an exit detection alert to an off-board recipient in response to receiving the exit detection alert signal from the exit detection sensor; and, if the exit detection sensor is positioned outside of the volume of space, to not transmit the exit detection alert to the off-board recipient in response to receiving the exit detection alert signal from the exit detection sensor.

2. The patient support apparatus of claim 1 further comprising a nurse call system interface adapted to communicate with a nurse call system outlet integrated into a wall of a healthcare facility, wherein the nurse call system outlet includes a plurality of electrical pins and wherein the controller is adapted to transmit the exit detection alert to the off-board recipient by changing an electrical state of a pin of the nurse call system outlet.

3. The patient support apparatus of claim 2 wherein the nurse call system interface is adapted to communicate with the nurse call system outlet by wireless or wired communication.

4. The patient support apparatus of claim 1 wherein the controller is further adapted to use radio frequency (RF) communication between the first transceiver and a second patient support apparatus to determine if the second patient support apparatus is positioned inside or outside of a second volume of space.

5. The patient support apparatus of claim 1 wherein the exit detection sensor includes a pressure sensing pad adapted to be positioned underneath the patient.

6. The patient support apparatus of claim 5 wherein the pressure sensing pad is positioned on a second support surface of second patient support apparatus.

7. The patient support apparatus of claim 1 wherein the first transceiver; is an ultra-wideband transceiver.

8. The patient support apparatus of claim 1 wherein the controller is further adapted to use RF communication between the first transceiver and a fixed locator to determine a position of the patient support apparatus relative to the fixed locator.

9. The patient support apparatus of claim 8 wherein the controller is further adapted to receive an identifier from the fixed locator, to determine if the patient support apparatus is positioned within a threshold distance to the fixed locator, and to forward the fixed locator identifier to a server if the patient support apparatus is positioned within the threshold distance.

10. A patient support apparatus comprising:

a support surface adapted to support a patient;

a display;

a first transceiver coupled to a first location on the patient support apparatus, the first transceiver adapted to wirelessly communicate with a second wireless transceiver coupled to a second patient support apparatus separate from the patient support apparatus;

and a controller adapted to use radio frequency (RF) communication between the first transceiver and the second patient support apparatus to determine a distance between the second patient support apparatus and the patient support apparatus; wherein the controller is further adapted to use the distance to determine if the second patient support apparatus is positioned inside or outside of a volume of space; to receive data from the second patient support apparatus; if the second patient support apparatus is positioned inside the volume of space, to perform at least one of the following: (a) to forward the data to an off-board recipient, or (b) to display the data on the display; and, if the second patient support apparatus is positioned outside the volume of space, to not perform (a) or (b).

11. The patient support apparatus of claim 10 wherein the controller is further adapted to receive an ID from the second patient support apparatus, to check to see if the ID matches a criterion, to forward the data to the off-board recipient if the ID matches the criterion and the second patient support apparatus is positioned inside the volume of space, and to not forward the data to the off-board recipient if the ID does not match the criterion.

12. The patient support apparatus of claim 10 wherein the data includes an exit detection alert signal.

13. The patient support apparatus of claim 12 further comprising a nurse call system interface adapted to communicate with a nurse call system outlet integrated into a wall of a healthcare facility, wherein the nurse call system outlet includes a plurality of electrical pins and wherein the controller is adapted to respond to the exit detection alert signal by changing an electrical state of a pin of the nurse call system outlet.

14. The patient support apparatus of claim 13 wherein the nurse call system interface is adapted to communicate with the nurse call system outlet by wireless or wired communication.

15. The patient support apparatus of claim 12 wherein the second patient support apparatus includes an exit detection sensor that includes a pressure sensing pad adapted to be positioned underneath the patient.

16. The patient support apparatus of claim 15 wherein the pressure sensing pad is adapted to be removable from the second patient support apparatus and positioned on a second support surface of another patient support apparatus.

17. The patient support apparatus of claim 10 wherein the patient support apparatus is a bed and the second patient support apparatus is a recliner.

18. The patient support apparatus of claim 10 wherein the data includes at least one of the following: a brake status of the second patient support apparatus, a lock status of a lock of the second patient support apparatus, an angle of a component of the second patient support apparatus, an error message, or an occupancy detection signal.

19. The patient support apparatus of claim 10 wherein the first transceiver is an ultra-wideband transceiver.

* * * * *